(12) United States Patent
Oki et al.

(10) Patent No.: US 11,507,842 B2
(45) Date of Patent: Nov. 22, 2022

(54) LEARNING METHOD, LEARNING APPARATUS, AND NON-TRANSITORY COMPUTER-READABLE STORAGE MEDIUM FOR STORING LEARNING PROGRAM

(71) Applicant: FUJITSU LIMITED, Kawasaki (JP)

(72) Inventors: Yusuke Oki, Kawasaki (JP); Koji Maruhashi, Hachioji (JP)

(73) Assignee: FUJITSU LIMITED, Kawasaki (JP)

(*) Notice: Subject to any disclaimer, the term of this patent is extended or adjusted under 35 U.S.C. 154(b) by 464 days.

(21) Appl. No.: 16/821,438

(22) Filed: Mar. 17, 2020

(65) Prior Publication Data

US 2020/0302305 A1 Sep. 24, 2020

(30) Foreign Application Priority Data

Mar. 20, 2019 (JP) .............................. JP2019-053570

(51) Int. Cl.
*G06N 3/08* (2006.01)
*G06N 5/04* (2006.01)
(Continued)

(52) U.S. Cl.
CPC ............... *G06N 3/084* (2013.01); *G06F 7/78* (2013.01); *G06F 17/16* (2013.01); *G06K 9/6215* (2013.01);
(Continued)

(58) Field of Classification Search
CPC ........ G06N 3/084; G06N 5/046; G06N 20/10; G06N 3/0454; G06N 3/0472; G06F 7/78; G06F 17/16; G06K 9/6215; G06K 9/6261; G06K 9/6232; G06V 10/764; G06V 10/765; G06V 10/7715; G06V 10/82; G06V 10/776; G16B 30/10; G16B 40/20

See application file for complete search history.

(56) References Cited

U.S. PATENT DOCUMENTS

2018/0018556 A1* 1/2018 Young .................... G06N 3/084
2018/0096247 A1 4/2018 Maruhashi
(Continued)

FOREIGN PATENT DOCUMENTS

JP 2018-055580 A 4/2018
WO 2007/102505 A1 9/2007

*Primary Examiner* — Juan A Torres
(74) *Attorney, Agent, or Firm* — Fujitsu Patent Center

(57) ABSTRACT

A learning method implemented by a computer, includes: creating an input data tensor including a local dimension and a universal dimension by partitioning series data into local units, the series data including a plurality of elements, each of the plurality of elements in the series data being logically arranged in a predetermined order; and performing machine learning by using tensor transformation in which a transformation data tensor obtained by transforming the input data tensor with a transformation matrix is outputted using a neural network, wherein the learning includes rearranging the transformation matrix so as to maximize a similarity to a matching pattern serving as a reference in the tensor transformation regarding the universal dimension of the input data tensor, and updating the matching pattern in a process of the machine learning regarding the local dimension of the input data tensor.

11 Claims, 30 Drawing Sheets

(51) Int. Cl.
 *G06N 20/10* (2019.01)
 *G06F 7/78* (2006.01)
 *G06K 9/62* (2022.01)
 *G06F 17/16* (2006.01)

(52) U.S. Cl.
 CPC .......... *G06K 9/6261* (2013.01); *G06N 5/046* (2013.01); *G06N 20/10* (2019.01)

(56) References Cited

U.S. PATENT DOCUMENTS

| | | | |
|---|---|---|---|
| 2018/0240243 A1* | 8/2018 | Kim | G06N 5/022 |
| 2019/0080235 A1* | 3/2019 | Maruhashi | G06N 3/08 |
| 2019/0080236 A1* | 3/2019 | Maruhashi | G06K 9/6262 |
| 2019/0087384 A1* | 3/2019 | Goto | G06N 20/00 |

* cited by examiner

FIG. 8

| LOCAL DIMENSION | UNIVERSAL DIMENSION | AMOUNT |
|---|---|---|
| b1 | e1 | 0 (=A) |
| b2 | e1 | 0 (=A) |
| b3 | e1 | 2 (=G) |
| b1 | e2 | 0 (=A) |
| b2 | e2 | 3 (=T) |
| b3 | e2 | 1 (=C) |
| b1 | e3 | 0 (=A) |
| b2 | e3 | 0 (=A) |
| b3 | e3 | 2 (=G) |
| b1 | e4 | 3 (=T) |
| b2 | e4 | 3 (=T) |
| b3 | e4 | 2 (=G) |
| b1 | e5 | 0 (=A) |
| b2 | e5 | 0 (=A) |
| b3 | e5 | 2 (=G) |
| b1 | e6 | 0 (=A) |
| b2 | e6 | 0 (=A) |
| b3 | e6 | 3 (=T) |
| b1 | e7 | 1 (=C) |
| b2 | e7 | 2 (=G) |
| b3 | e7 | 3 (=T) |
| b1 | e8 | 0 (=A) |
| b2 | e8 | 2 (=G) |
| b3 | e8 | 0 (=A) |

FIG. 12

|    | b1  | b2  | b3  | e1 | e2 | e3 | e4 | e5 | e6 | e7 | e8 |
|----|-----|-----|-----|----|----|----|----|----|----|----|----|
| e'8 | 0   | 0   | 0   | 0  | 0  | 0  | 0  | 0  | 0  | 0  | 1  |
| e'7 | 0   | 0   | 0   | 0  | 0  | 0  | 0  | 0  | 0  | 1  | 0  |
| e'6 | 0   | 0   | 0   | 0  | 0  | 0  | 0  | 0  | 1  | 0  | 0  |
| e'5 | 0   | 0   | 0   | 0  | 0  | 0  | 0  | 1  | 0  | 0  | 0  |
| e'4 | 0   | 0   | 0   | 0  | 0  | 0  | 1  | 0  | 0  | 0  | 0  |
| e'3 | 0   | 0   | 0   | 0  | 0  | 1  | 0  | 0  | 0  | 0  | 0  |
| e'2 | 0   | 0   | 0   | 0  | 1  | 0  | 0  | 0  | 0  | 0  | 0  |
| e'1 | 0   | 0   | 0   | 1  | 0  | 0  | 0  | 0  | 0  | 0  | 0  |
| b'3 | 0/1 | 0/1 | 0/1 | 0  | 0  | 0  | 0  | 0  | 0  | 0  | 0  |
| b'2 | 0/1 | 0/1 | 0/1 | 0  | 0  | 0  | 0  | 0  | 0  | 0  | 0  |
| b'1 | 0/1 | 0/1 | 0/1 | 0  | 0  | 0  | 0  | 0  | 0  | 0  | 0  |

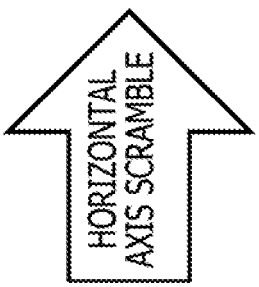

FIG. 28
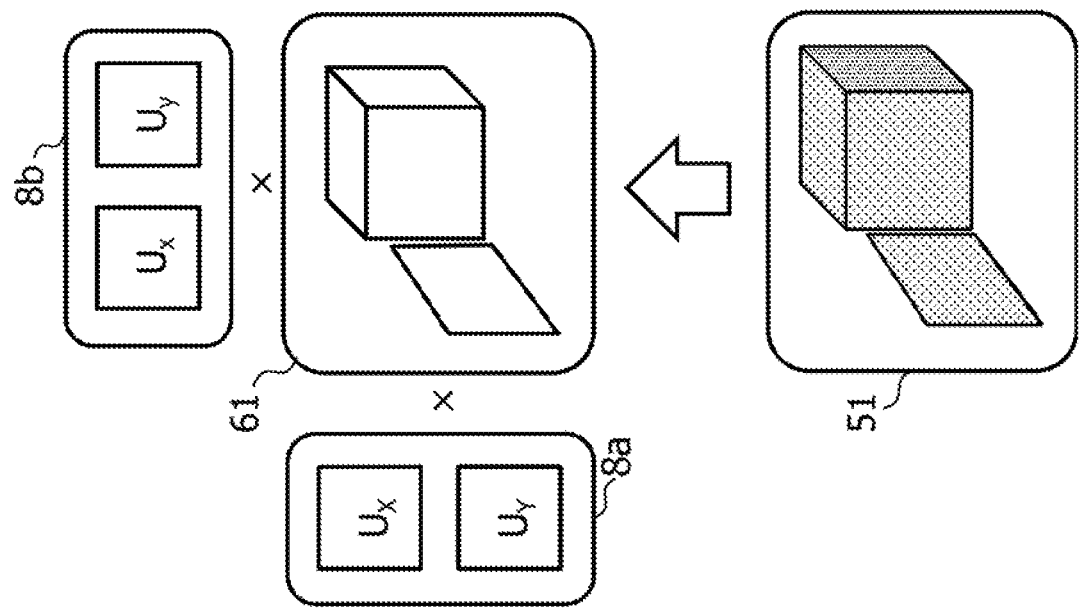
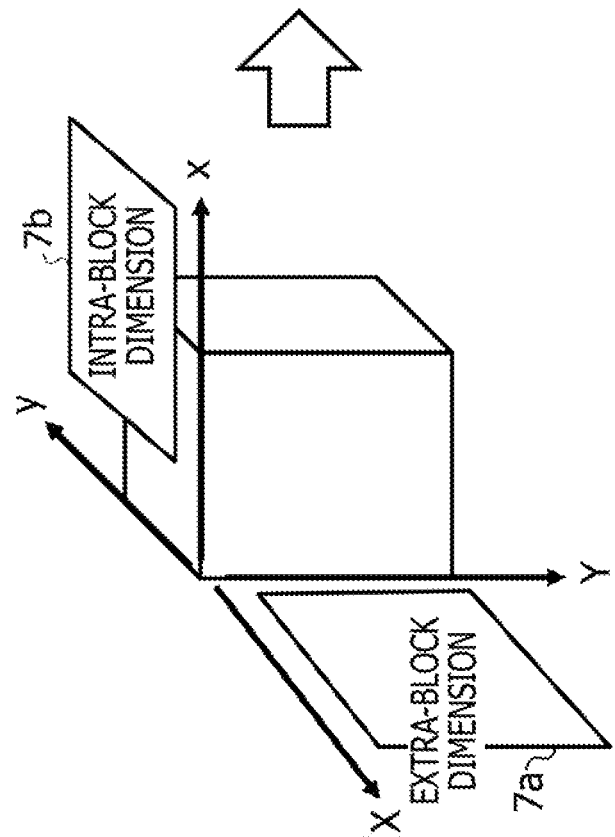

FIG. 29A
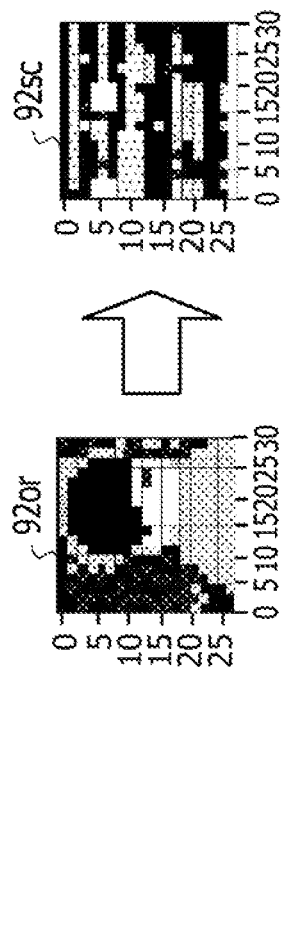
FIG. 29B
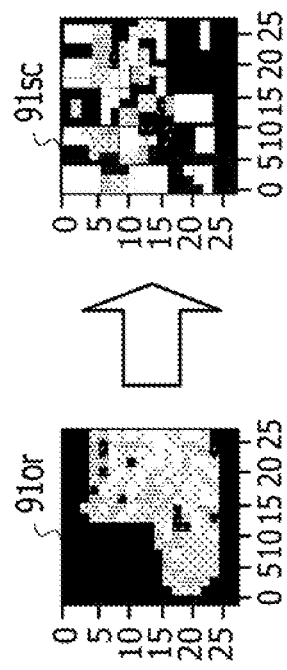
FIG. 29C
| CLASSIFICATION METHOD | FASHION MNIST (10 CLASS) | CMU FACES IMAGES (4 CLASS) |
|---|---|---|
| EMBODIMENT | 0.75 | 0.818 |
| CNN WITH ADJUSTED STRIDE | 0.651 | 0.560 |
| HISTOGRAM FORMATION + SVM | 0.595 | 0.309 |

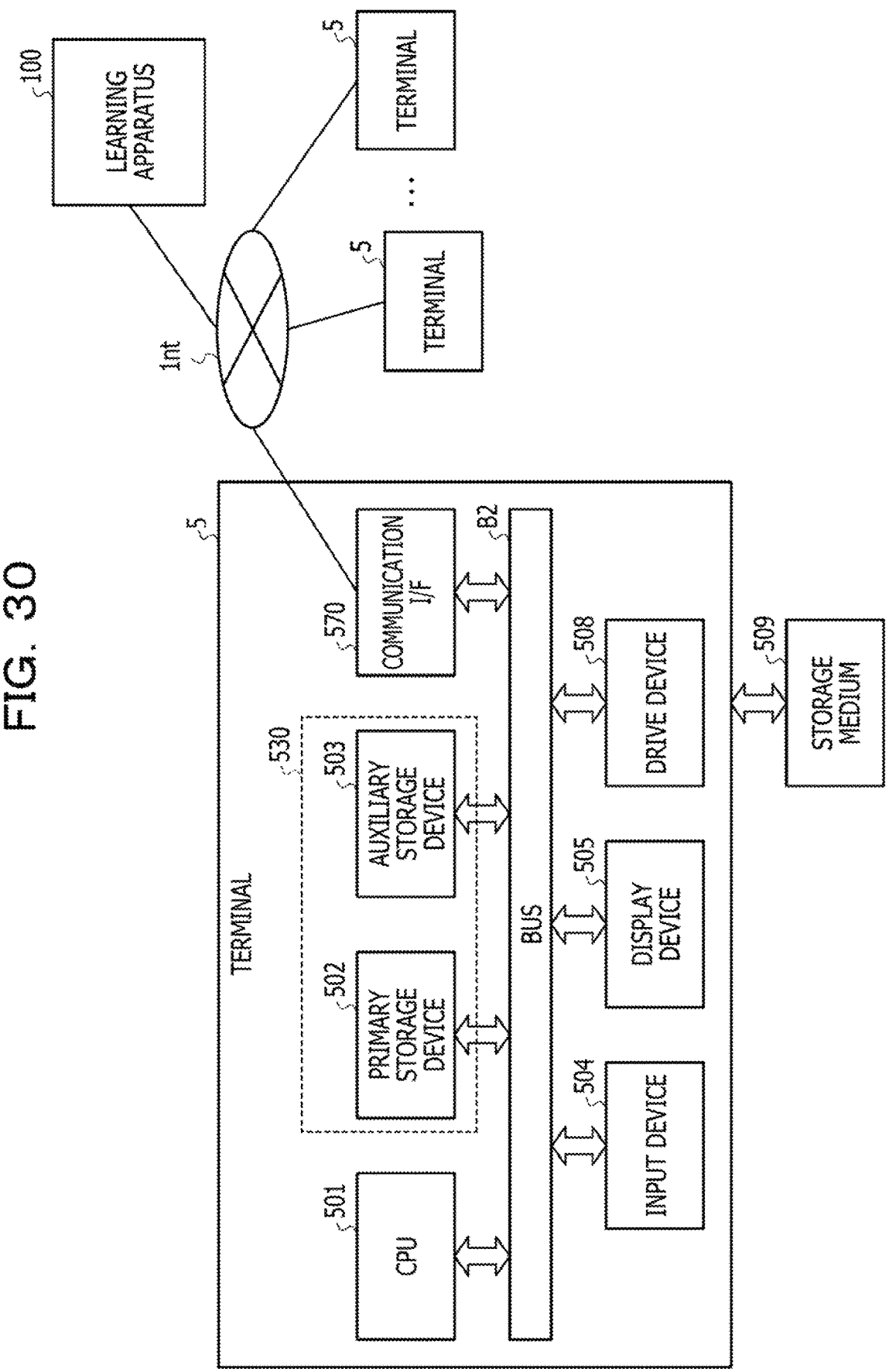

LEARNING METHOD, LEARNING APPARATUS, AND NON-TRANSITORY COMPUTER-READABLE STORAGE MEDIUM FOR STORING LEARNING PROGRAM

CROSS-REFERENCE TO RELATED APPLICATION

This application is based upon and claims the benefit of priority of the prior Japanese Patent Application No. 2019-53570, filed on Mar. 20, 2019, the entire contents of which are incorporated herein by reference.

FIELD

The embodiments discussed herein are related to a learning method, a learning apparatus, and a non-transitory computer-readable storage medium for storing a learning program.

BACKGROUND

Neural network-based machine learning has been increasingly used in various fields in recent years. Input data formats in the machine learning vary depending on the fields. Various ingenuities have been applied in order to obtain learning results more accurately.

One known technique is to form time-series data by arranging audio feature parameters obtained by performing an audio feature analysis of infant cry data, and then to subject the time-series data of the audio feature parameters to learning processing of a distribution of audio feature parameters for each emotion and each audio feature segment.

Examples of the related art include International Publication Pamphlet No. WO 2007/102505 and Japanese Laid-open Patent Publication No. 2018-55580.

SUMMARY

According to an aspect of the embodiments, a machine learning method implemented by a computer, includes: creating an input data tensor including a local dimension and a universal dimension by partitioning series data into local units, the series data including a plurality of elements, each of the plurality of elements in the series data being logically arranged in a predetermined order; and performing machine learning by using tensor transformation in which a transformation data tensor obtained by transforming the input data tensor with a transformation matrix is outputted using a neural network, wherein the machine learning includes rearranging the transformation matrix so as to maximize a similarity to a matching pattern serving as a reference in the tensor transformation regarding the universal dimension of the input data tensor, and updating the matching pattern in a process of the machine-learning regarding the local dimension of the input data tensor.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 8 illustrates an example of creating an input data tensor;

FIG. 12 illustrates an example of an ordering transformation matrix;

FIGS. 27A, 27B, and 27C are diagrams for explaining a method of creating the scrambled image;

FIG. 28 is a diagram for explaining dimension partitioning of the scrambled image;

FIGS. 29A, 29B, and 29C illustrate a comparative example of classification accuracy; and FIG. 30 illustrates an example of a network system.

DESCRIPTION OF EMBODIMENT(S)

The machine learning involves a convolution layer that extracts features of inputted data and a pooling layer that summarizes the extracted features. The convolution layer extracts multiple features in predetermined units while the pooling layer determines a representative feature in each predetermined unit.

As described above, the pooling layer determines the representative feature by focusing on a particular local range. Accordingly, this configuration may fail accurate classification of certain data if the data includes multiple local features which represent a distinct feature as a whole when combined together.

Given the situation, an object of an aspect of this disclosure is to enable appropriate learning of series data having both a local feature and a universal feature.

This aspect enables appropriate machine learning of series data having both a local feature and a universal feature.

Figure 1:
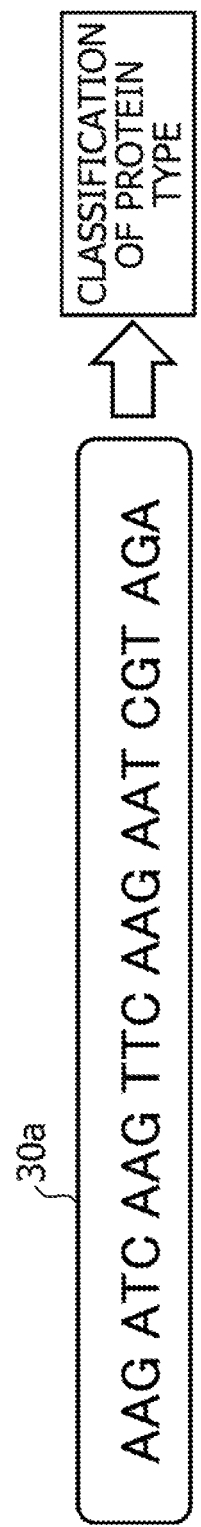
FIG. 1 illustrates an example of series data.

Hereinafter, an embodiment of the present disclosure is described with reference to the drawings. A gene sequence is an example of series data in which the order of elements is defined. The gene sequence is characterized by a combination of multiple local features. A description is given of machine learning in a case of classifying the gene sequence as illustrated in FIG. 1. Noted that the machine learning may be referred to as "learning", "machine learning processing", and the like. For example, the machine learning apparatus may be referred to as "learning apparatus", "learning-apparatus", and the like.

FIG. 1 illustrates an example of series data. Series data 30a illustrated in FIG. 1 represents a gene sequence "AAG ATC AAG TTC AAG AAT CGT AGA". This gene sequence is classified into a protein type. Determination of a protein type is described with reference to FIG. 2.

Figure 2:
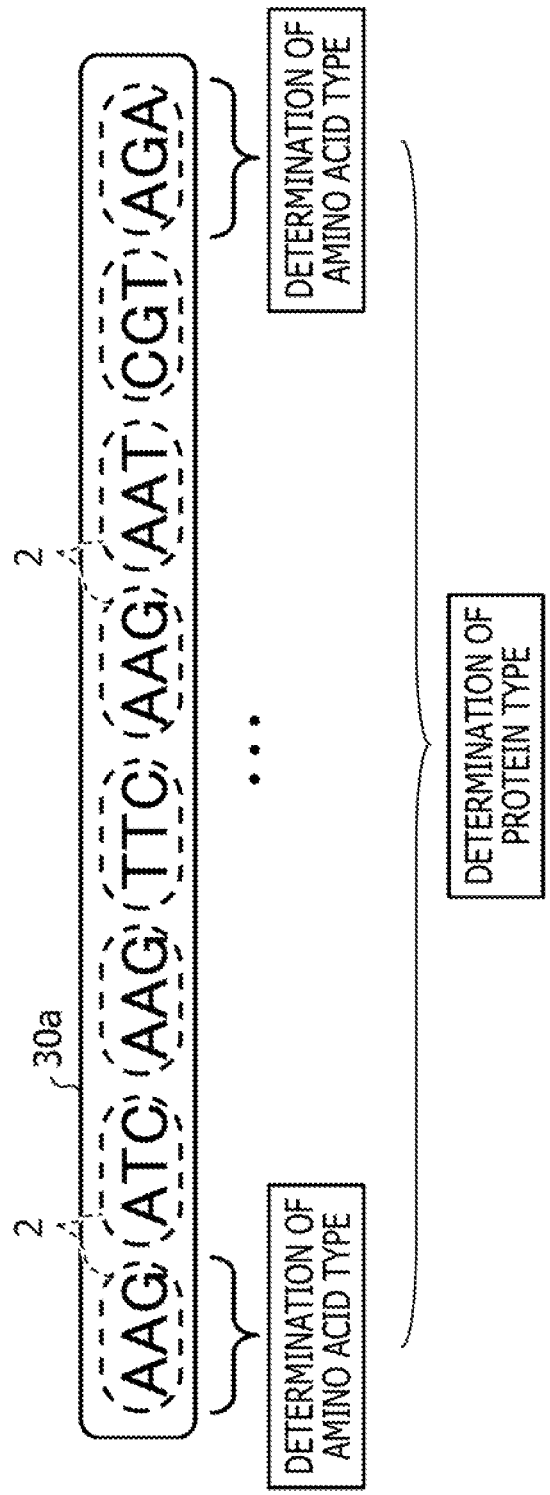
FIG. 2 is a diagram for explaining determination of a protein type.

FIG. 2 is a diagram for explaining determination of a protein type. According to FIG. 2, the gene sequence in FIG. 1 determines the protein type based on a composition of amino acids. In the gene sequence, each codon 2 including an array of three bases indicates a type of an amino acid. The bases representing the gene sequence include four types, namely, adenine (A), cytosine (C), guanine (G), and thymine (T). Each amino acid has a distinct feature and a combination of such amino adds therefore brings about a distinct feature of each gene sequence.

The type of each amino acid created by a corresponding codon 2 is determined based on a "local feature" and the type of a protein created by a combination of multiple amino adds is determined based on a "universal feature". Likewise, regarding target data that includes units each representing a certain feature and is further classified by a feature derived from a combination of the certain features, the certain feature in each predetermined unit (or in each predetermined range) is referred to as the "local feature" while the feature to be determined based on the combination of the local features is referred to as the "universal feature".

With reference to FIG. 2, the respective codons "AAG", "ATC", "AAG", "TTC", "AAG", "AAT", "CGT", and "AGA" in the gene sequence of the series data 30a determine corresponding types of amino acids. And it is an appropriate approach to determine the type of the protein based on the eight types of the amino acids thus determined. Machine learning for determining the protein type has been known as a gene analysis. The gene analysis is briefly explained by using the gene sequence of the series data 30a as an example.

Figure 3:
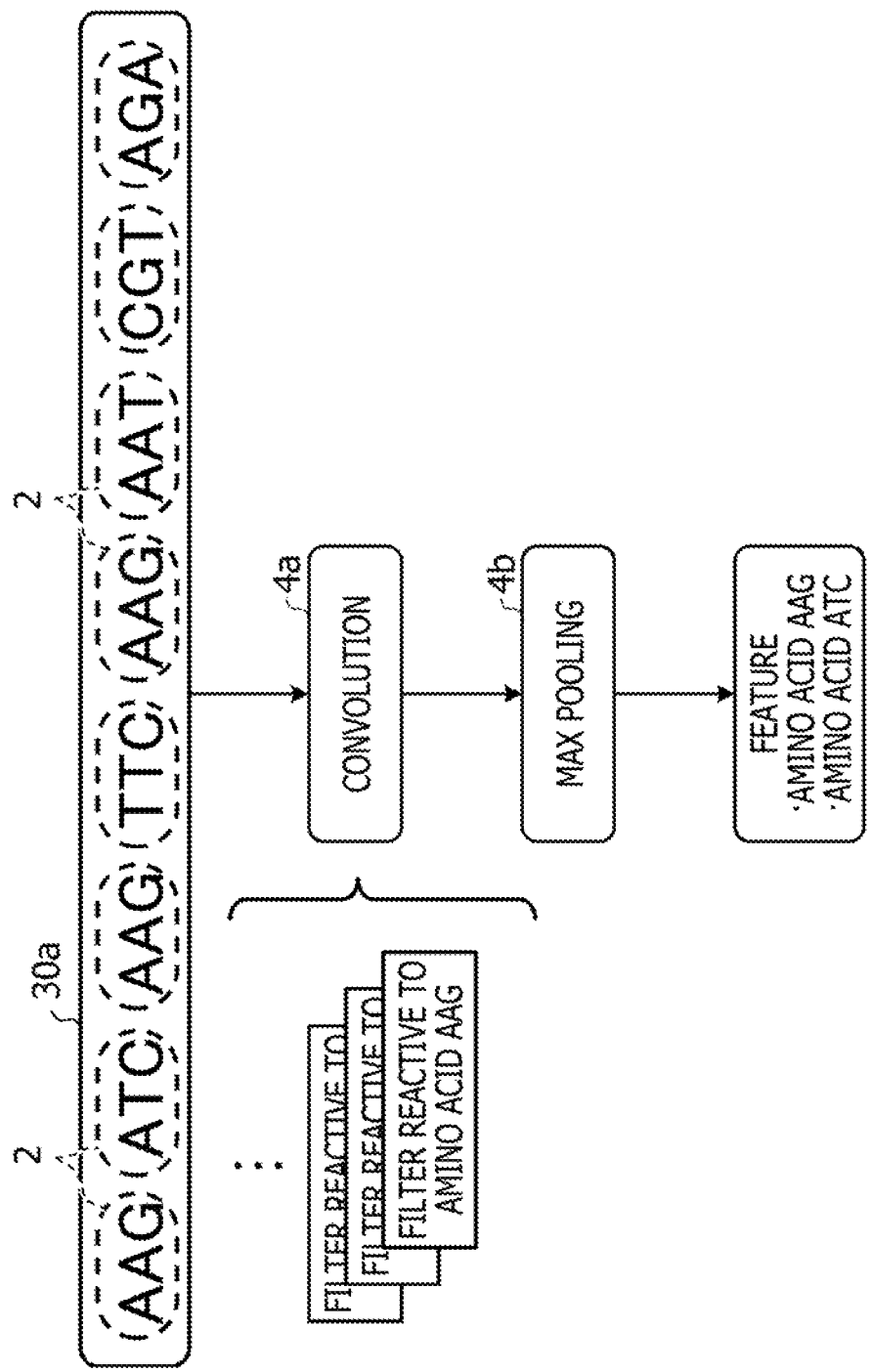
FIG. 3 is a diagram for explaining a first example of a gene analysis.

FIG. 3 is a diagram for explaining a first example of a gene analysis. The gene analysis illustrated in FIG. 3 describes a case of conducting the machine learning based on a convolution layer 4a and a pooling layer 4b. Using filters that react to base sequences of respective amino adds, the convolution layer 4a subjects the codons 2 selected in turn from the series data 30a to convolution with the filters, thereby extracting features of the codons 2. The pooling layer 4b extracts the feature that reacts most to each of the filters regarding each of the codons 2.

The processing using the convolution layer 4a and the pooling layer 4b is repeatedly conducted in response to a length of the gene sequence, that is, the number of the codons 2 in the series data 30a. Thus, amino acids that react most in the series data 30a are outputted as features of the protein. In this example, amino acids "AAG" and "ATC" are outputted.

However, if there is another protein which involves a different series data 30a from the gene sequence illustrated in FIG. 3 but still includes the amino acids "AAG" and "ATC" that are bonded in its gene sequence as its major codons 2, then this protein indicates the same result. In this case, it is not possible to classify these proteins appropriately. The series data 30a in FIG. 3 represents a protein which includes three pieces of the amino acid "AAG" that are bonded to other amino acids. Nonetheless, the other protein including three pieces of this amino add though having different bonds represents a different feature but the pooling layer 4b still lumps the features of the codons of the same type together as one feature. In this regard, the pooling layer 4b is prone to complicate distinctive learning of these proteins.

Here, a possible solution is to extract a sequence of the bases representing a feature of a protein by using the number of the bases to be combined as a prescribed unit instead of adopting the codons 2 (that is, sets of three consecutive bases) as the prescribed unit. The above-described extraction processing is referred to as a "combination search".

Figure 4:
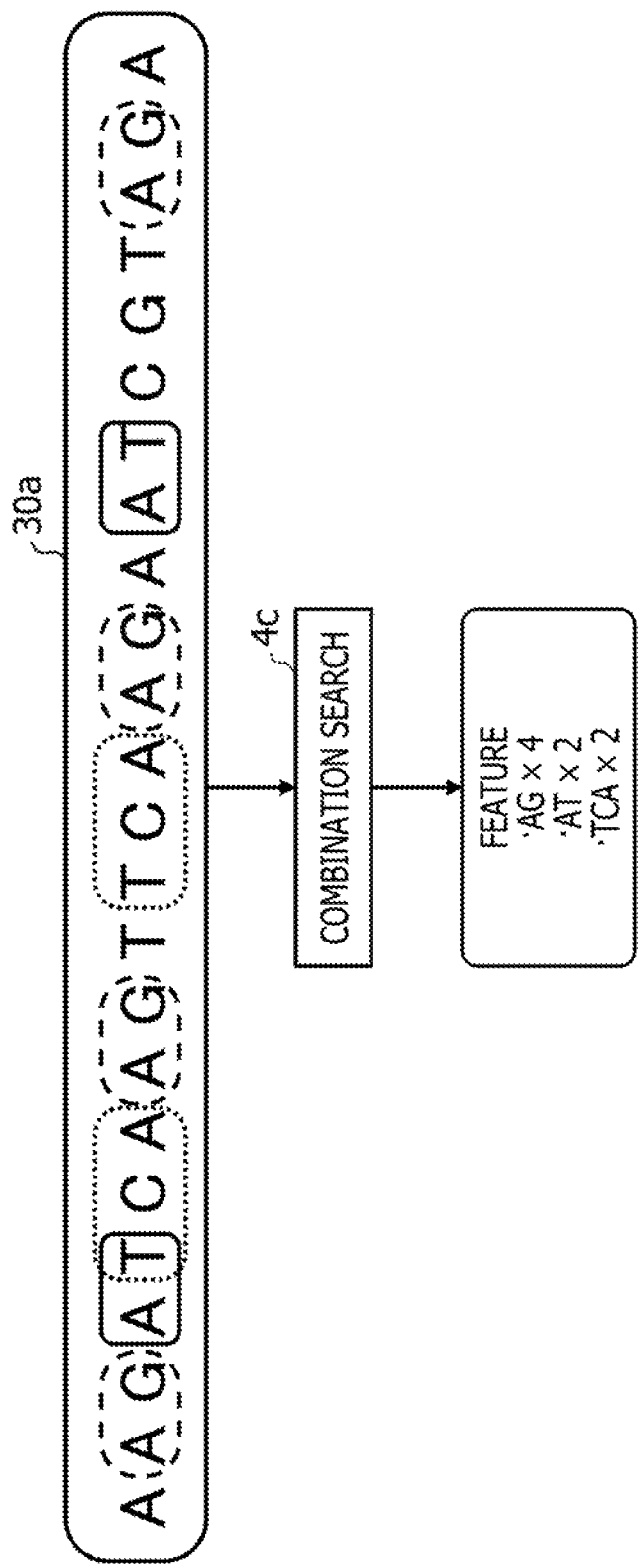
FIG. 4 is a diagram for explaining a second example of the gene analysis.

FIG. 4 is a diagram for explaining a second example of the gene analysis. In FIG. 4, a combination search 4c learns main bonds of the bases as features by learning series data 3a while determining the optimal order of input to a neural network.

The combination search 4c is a technique developed by the applicant, which aims to improve learning accuracy by taking into account a correspondence relation between each of input values included in input data with each of nodes (representing neurons) on an input layer of a neural network. This technique is called "Deep Tensor" because the combination search 4c learns optimal correspondence relations of the multiple input values with the multiple nodes. In Deep Tensor, a tensor representing the input data is subjected to transformation (tensor transformation) so as to establish the optimal correspondence relations before inputting the input values to the neural network and the transformed tensor is used for learning.

Depending the input data format, an ingenuity may be desirable for adaptation to Deep Tensor. Taking a case where the input data is the gene sequence as an example, a description is given below of a case of simply applying the input data itself to Deep Tensor.

FIG. 4 illustrates that the combination search 4c extracts a combination "AG" at four locations, a combination "AT" at two locations, and a combination "TCA" at two locations as features of the gene sequence. Unlike the result of FIG. 3, this result enables learning of main bonds of bases as universal features of the gene sequence. However, the combination search 4c is not designed to search all the combinations. Accordingly, features attributed to the order of arrangement of locals (which are the amino acids in this example) are lost in this case.

Given the situation, it is thought to be appropriate to learn with the technique of the first example (FIG. 3) based on the gene analysis in the case of emphasizing the local features or to learn with the technique of the second example (FIG. 4) based on the learning by use of Deep Tensor in the case of emphasizing the universal combinations of features. In this case, however, a person with relevant knowledge is supposed to comprehensively analyze the respective results of learning, which is not practical.

As mentioned earlier, there is series data having both a local feature and a universal feature such as the gene sequence. A technique that enables to obtain a result at high accuracy even from the above-mentioned series data by using Deep Tensor is discussed below.

Figure 5:
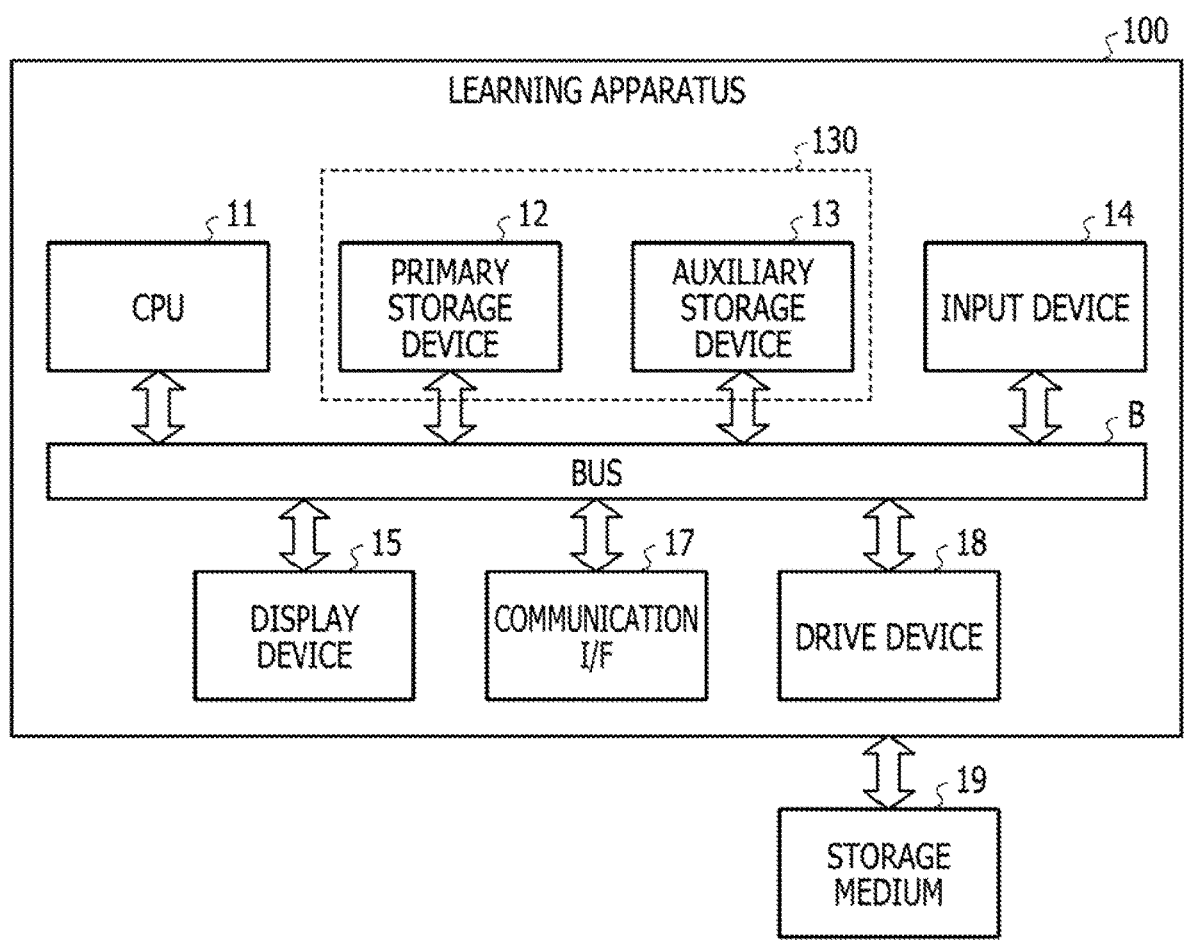
FIG. 5 illustrates a hardware configuration example of a learning apparatus.

FIG. 5 illustrates a hardware configuration example of a learning apparatus. According to FIG. 5, a learning apparatus 100 is an information processing apparatus, and includes a central processing unit (CPU) 11, a primary storage device 12, an auxiliary storage device 13, an input device 14, a display device 15, a communication I/F 17, and a drive device 18, which are coupled with a bus B. The auxiliary storage device 13, the input device 14, and an external storage device to which the learning apparatus 100 is accessible are collectively referred to as a storage unit 130.

The CPU 11 corresponds to a processor that controls the learning apparatus 100, and implements various processes according to this embodiment described below by executing a program stored in the storage unit 130. The input device 14 is operated by a user and inputs data in response to the operation, and the display device 15 serves as a use interface and displays various screens. The communication I/F 17 controls communication with an external device.

A learning program according to this embodiment stored in a storage medium 19 (for example, a compact disc read-only memory (CD-ROM)) is installed on the storage unit 130 via the drive device 18 and is thus rendered executable by the CPU 11.

The storage medium 19 for storing the program according to this embodiment is not limited to the CD-ROM, and it may be any one or more non-transitory and tangible media having a computer-readable structure. As a computer-readable storage medium, in addition to the CD-ROM, a digital versatile disk (DVD), a portable recording medium such as a Universal Serial Bus (USB) memory, and a semiconductor memory such as a flash memory may be used.

Figure 6:
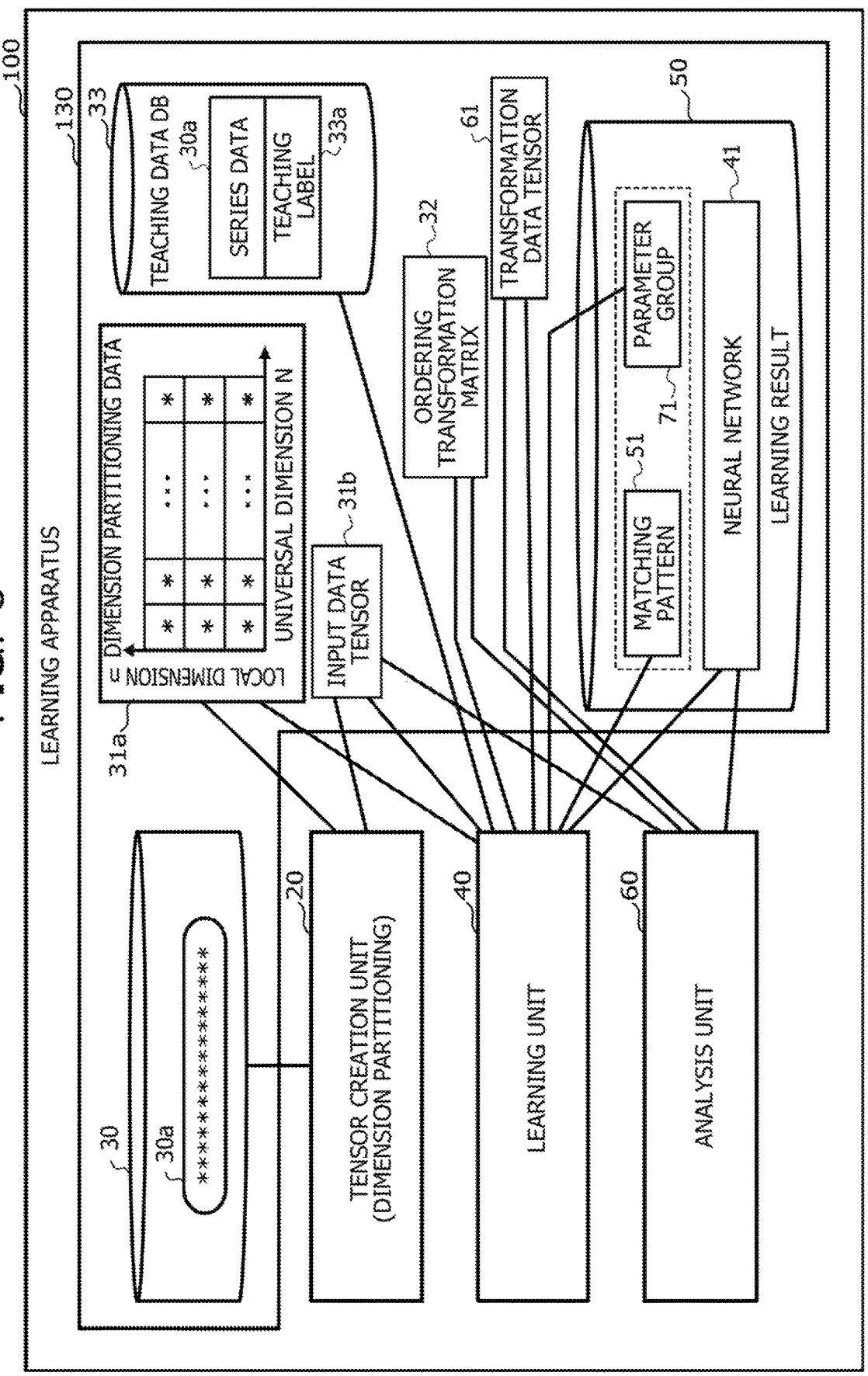
FIG. 6 illustrates a functional configuration example of the learning apparatus.

FIG. 6 illustrates a functional configuration example of the learning apparatus. In FIG. 6, the learning apparatus 100 includes a tensor creation unit 20, a learning unit 40, and an analysis unit 60. The tensor creation unit 20, the learning unit 40, and the analysis unit 60 are implemented by processing which the program installed on the learning apparatus 100 causes the CPU 11 to execute. The storage unit 130 stores input data 30, dimension partitioning data 31a, an input data tensor 31b, an ordering transformation matrix 32, a teaching data DB 33, a learning result 50, a transformation data tensor 61, and the like.

When the tensor creation unit 20 accepts the series data 30a as the input data 30, the tensor creation unit 20 creates the dimension partitioning data 31a by partitioning the series data 30a into a local dimension and a universal dimension. The tensor creation unit 20 creates the input data tensor 31b by using the dimension partitioning data 31a thus created. A method of creating the input data tensor 31b relevant to the series data 30a is discussed later.

The tensor creation unit 20 creates the input data tensor 31b relevant to the series data 30a in the course of learning processing by the learning unit 40 and in the course of analysis processing by the analysis unit 60, respectively. The teaching data DB 33 that stores the series data 30a provided with a teaching label 33a in advance is used in the course of the learning processing. The series data 30a inputted by the user serves as the input data 30 in the course of the analysis processing.

The learning unit 40 learns a neural network 41 as well as a matching pattern 51 to optimize the order of input of the input data tensor 31b created by the tensor creation unit 20 to the neural network 41.

Figure 9:
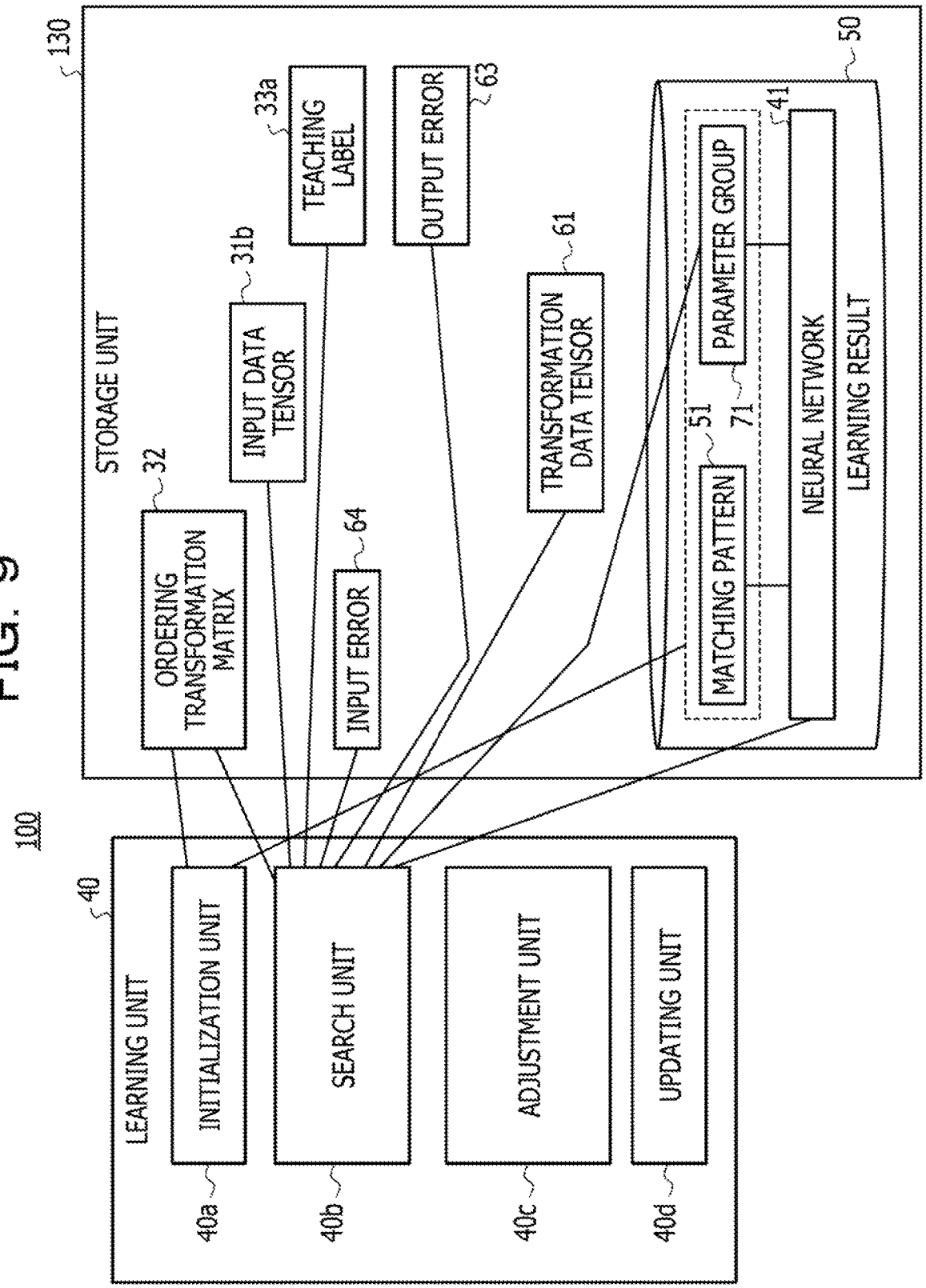
FIG. 9 is a first diagram for explaining a functional configuration example of a learning unit.
Figure 10:
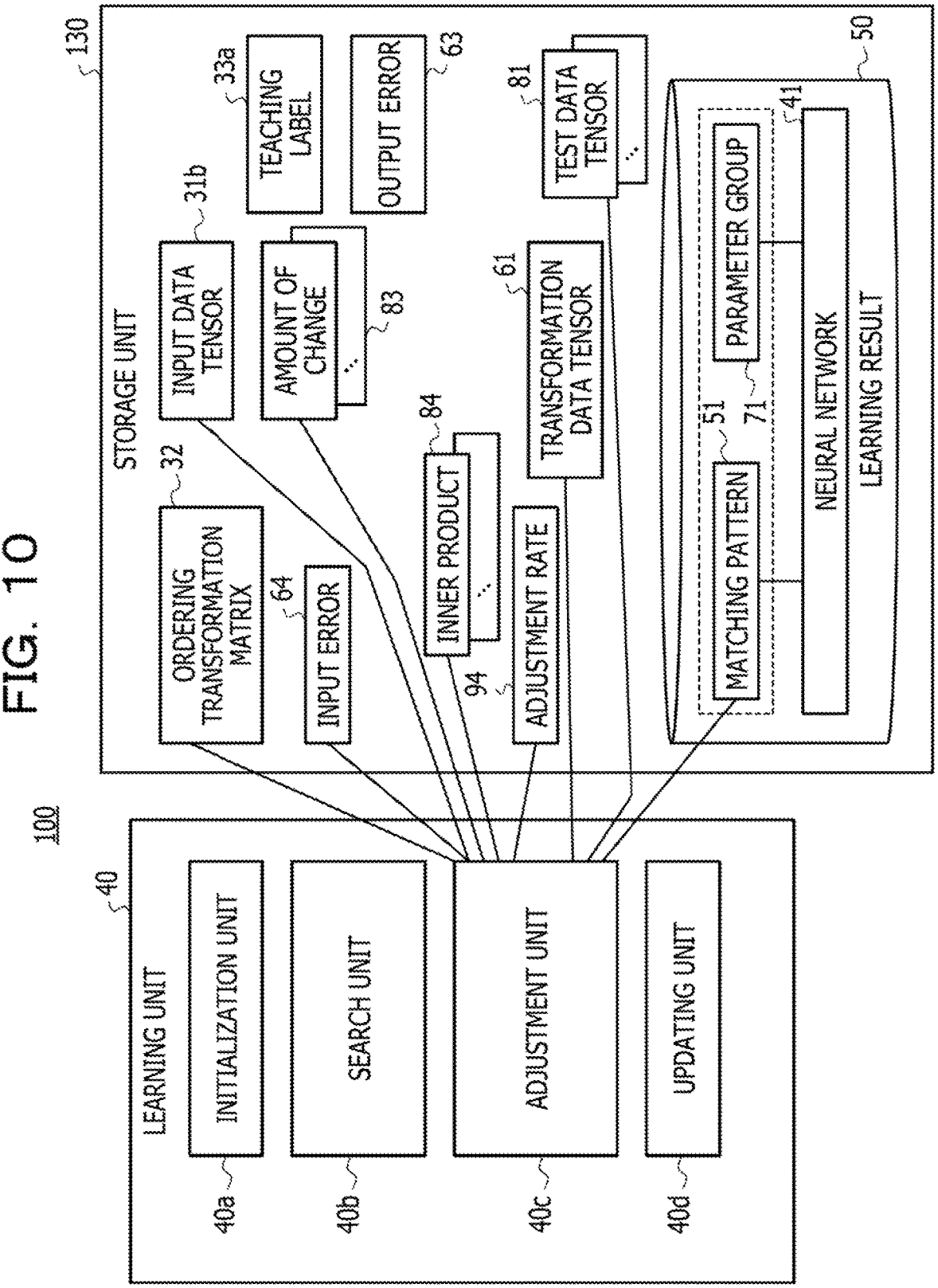
FIG. 10 is a second diagram for explaining the functional configuration example of the learning unit.
Figure 11:
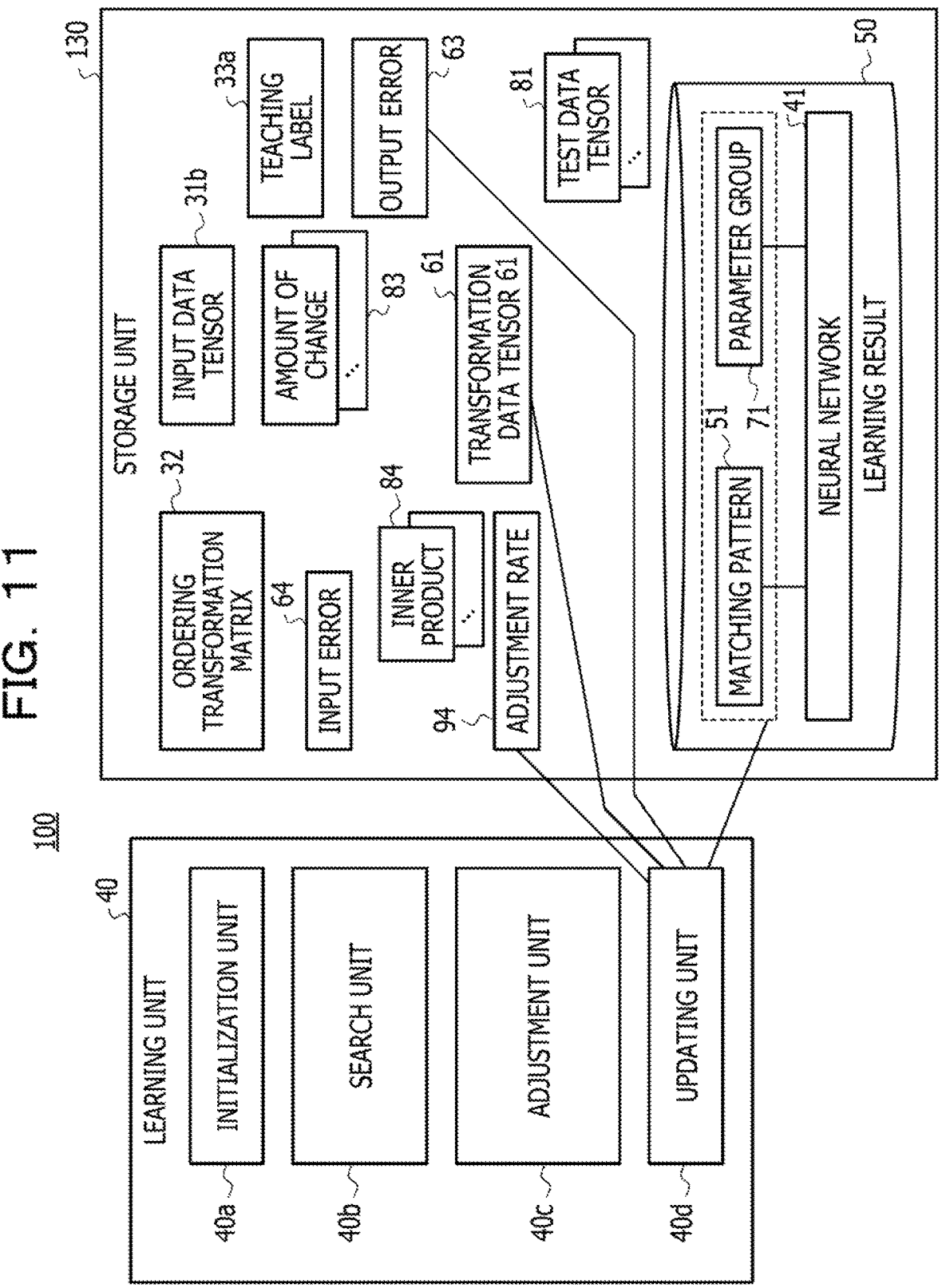
FIG. 11 is a third diagram for explaining the functional configuration example of the learning unit.

The learning unit 40 creates the transformation data tensor 61 by changing the order of input to the input data tensor 31b so as to maximize a similarity to the matching pattern 51 that is adjusted based on an input error 64 (FIGS. 9 to 11). The order of input is optimized by adjusting the matching pattern 51, and the transformation data tensor 61 turns into a tensor for a high-accuracy analysis which is applicable to arbitrary input data tensor 31b for achieving an analysis at high accuracy, thereby improving learning accuracy.

In this embodiment, Deep Tensor designed to learn the matching pattern 51 for obtaining the transformation data tensor 61 to achieve the analysis at high accuracy by transforming the input data tensor 31b is carried out in the learning while using the neural network 41. A parameter group 71 for the neural network 41 is optimized by the learning while using Deep Tensor.

The analysis unit 60 creates the most similar transformation data tensor 61 to the matching pattern 51 from the input data tensor 31b created by the tensor creation unit 20 while using the ordering transformation matrix 32, and classifies the input data 30 with the neural network 41.

Figure 7:
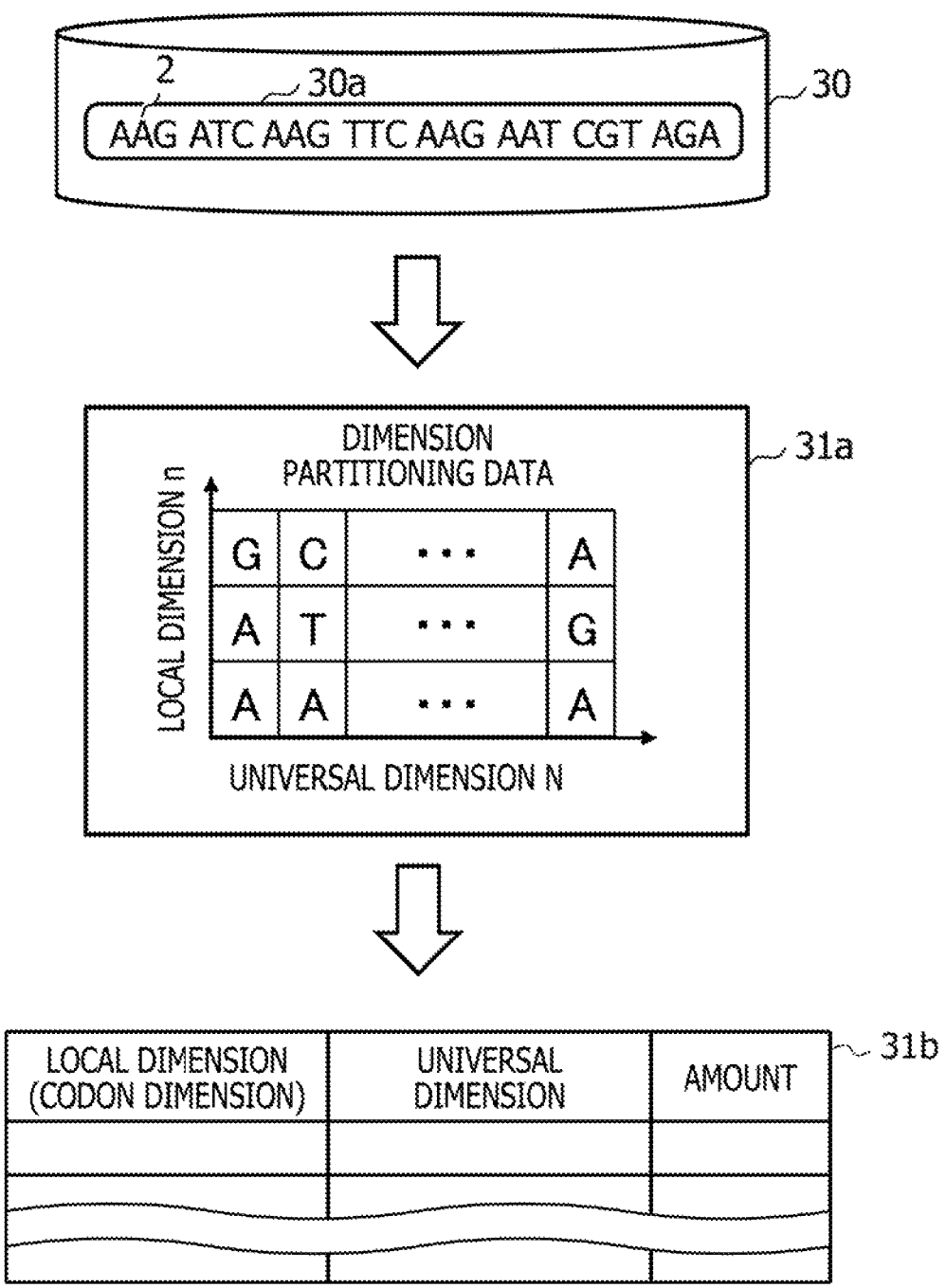
FIG. 7 is a diagram for explaining an outline of tensor creation processing by a tensor creation unit.

FIG. 7 is a diagram for explaining an outline of tensor creation processing by a tensor creation unit. In FIG. 7, the tensor creation unit 20 partitions the dimension of the series data 30a which is the input data 30.

When the series data 30a is the gene sequence that represents a protein by using the sequence of the codons 2, the tensor creation unit 20 sequentially arranges three bases in a local dimension along a vertical axis for the respective the codons 2 and arranges units of the codons 2 in accordance with the order of appearance in a universal dimension along a horizontal axis. In the following explanation using the example of the gene sequence, such an exemplary local dimension may be referred to as a "codon dimension" when appropriate. Each codon 2 constitutes a local unit for creating the local dimension. The dimension partitioning data 31a with the arrangement of the local dimension and the universal dimension thus created is stored in the storage unit 130.

The tensor creation unit 20 further creates the input data tensor 31b by using the dimension partitioning data 31a thus created. The input data tensor 31b is a list that indicates all the combinations of the codon dimension and the universal dimension, in which an amount obtained by a predetermined calculation method is set to each combination.

Assuming that a codon dimension n represents the number of bases for each codon and a universal dimension N represents the number of the codons 2 indicated in the series data 30a, the value n is equal to 3 and the value N is equal to 8 in this example. As a consequence, the input data tensor 31b is a tensor that involves 24 (=3×8) combinations. An example of creating the input data tensor 31b is illustrated in FIG. 8.

FIG. 8 illustrates the example of creating the input data tensor. According to FIG. 8, the input data tensor 31b is a tensor that indicates an amount for each combination of a codon dimension and a universal dimension.

In terms of the codon dimension (i.e., the local dimension),
b1 represents "AAATAACA",
b2 represents "ATATAAGG", and
b3 represents "GCGCGTTA".
In terms of the universal dimension, e1 represents "AAG",
e2 represents "ATC",
e3 represents "AAG",
e4 represents "TTC",
e5 represents "AAG",
e6 represents "AAT",
e7 represents "CGT", and
e8 represents "AGA".

Since the dimension partitioning data 31a is in a matrix format, one base is designated by a local dimension and a universal dimension. An amount corresponding to the designated base is associated with the combination of the local dimension and the universal dimension. Any one features unique to the base such as the number of atoms of the designated base and the molar mass thereof may be used as the set amount. For the sake of simplifying the explanation, the amount of A (adenine) is set to "0", the amount of C (cytosine) is set to "1", the amount of G (guanine) is set to "2", and the amount of T (thymine) is set to "3" in the following description.

Specifically, the combination of the local dimension b1 and the universal dimension e1 designates the base "A" based on the dimension partitioning data 31a and the amount is therefore set to "0". In a case that the combinations and the relevant amounts are expressed in the format of (local dimension, universal dimension, amount), these parameters are expressed as follows:

(b1, e1, 0);
(b2, e1, 0);
(b3, e1, 2);
(b1, e2, 0);
(b2, e2, 3);
(b3, e2, 1);
. . .
(b1, e8, 0);
(b2, e8, 2); and
(b3, e8, 0).

Noted that the input data tensor 31b representing these pieces of data (i.e., (b1, e1, 0) . . . (b3, e8, 0)) is created in the storage unit 130.

FIGS. 9 to 11 are diagrams for explaining a functional configuration example of the learning unit. According to FIGS. 9 to 11, the learning unit 40 includes an initialization unit 40a, a search unit 40b, an adjustment unit 40c, and an updating unit 40d.

According to FIG. 9, the initialization unit 40a initializes the ordering transformation matrix 32, the matching pattern 51, and the parameter group 71.

Regarding the universal dimension of the input data tensor 31b, the search unit 40b determines the ordering transformation matrix 32 so as to maximize the similarity to the matching pattern 51, and obtains the input error 64 by performing forward propagation and back propagation involving the neural network 41. The ordering transformation matrix 32 is discussed later.

Specifically, the search unit 40b transposes the order of input of the input data tensor 31b to be applied to the learning by using the local dimension while setting the common universal dimension, thus determining the ordering transformation matrix 32 based on the amounts so as to maximize the similarity to the matching pattern 51. As a consequence of transposing the order of input, the transformation data tensor 61 is created in the storage unit 130.

The transformation data tensor 61 is a tensor obtained by transposing the order of combinations of the local dimension with the universal dimension. When the tensor is regarded as a table, the aforementioned operation corresponds to the transposition of the order of records. The order of input of nodes on an input layer of the neural network 41 is determined in advance. Classification results are obtained by sequentially inputting the amounts from the combinations on a higher layer in the transformation data tensor 61 to the nodes of the neural network 41. This operation is called "forward propagation".

Moreover, the search unit 40b calculates an output error 63 between each classification result thus obtained and the teaching label 33a, and obtains the input error 64 by multiplying the output error 63 by each parameter wi in the parameter group 71. This operation is called "back propagation".

According to FIG. 10, the adjustment unit 40c obtains an amount of change 83 from the ordering in the transformation data tensor 61 depending on each shuffling of the order of input of the input data tensor 31b by using the universal dimension, then calculates an average of inner products 84 of the obtained amounts of change 83 and the input errors 64, thereby setting an adjustment rate 94 applicable to the ordering of the local dimension.

Specifically, the adjustment unit 40c creates a test data tensor 81 depending on each shuffling of the order of input of the input data tensor 31b by using the universal dimension so as to maximize the similarity to the matching pattern 51, and obtains a difference in amount between each of the created test data tensors 81 and the transformation data tensor 61. The difference in amount for each rearrangement of the order of input thus obtained is stored as the amount of change 83 in the storage unit 130.

Next, the adjustment unit 40c obtains the adjustment rate 94 by calculating the inner products 84 of the respective amounts of change 83 and the input error 64 and then averaging the inner products 84. The obtained adjustment rate 94 is stored in the storage unit 130.

According to FIG. 11, the updating unit 40d updates the parameter group 71 and the matching pattern 51. Specifically, the updating unit 40d updates the parameter group 71 based on the transformation data tensor 61 and the output error 63 between the learning result by the forward propagation and the teaching label 33a. The updating unit 40d updates the matching pattern 51 by using the adjustment rate 94. The updating method by the updating unit 40d is discussed later.

A description is given of an example of the ordering transformation matrix 32. FIG. 12 illustrates the example of the ordering transformation matrix. The ordering transformation matrix 32 is a matrix to represent the correspondence relations in the universal dimension and the correspondence relations in the local dimension while fixing the rest of the correspondence relations, that is, the correspondence relations of the universal dimension with the local dimension to 0.

The ordering transformation matrix 32 of FIG. 12 is a matrix created from the input data tensor 31b of FIG. 8. In the input data tensor 31b, codon dimension elements are indicated with b1, b2, and b3 while universal dimension elements are indicated with e1, e2, . . . , e8. Meanwhile, at a transformation destination, codon dimension elements are indicated with b'1, b'2, and b'3 while universal dimension elements are indicated with e'1, e'2, . . . , e'8. Numerals (1, 2, 3, . . . ) in the elements at the transformation destination indicate locations in the tensor. Here, a smaller numeral is assumed to be earlier in terms of the order of input.

A universal dimension matrix 32a representing the correspondence relations in the universal dimension designates elements associated with the same position in an initial state.

Likewise, a local dimension matrix 32b representing the correspondence relations in the local dimension also designates elements associated with the same position in the initial state.

The correspondence relations among the elements in the universal dimension matrix 32a are determined by setting the ordering transformation matrix 32 by the search unit 40b such that the amounts in the input data tensor 31b become most similar to the matching pattern 51. The correspondence relations among the elements the local dimension matrix 32b are determined as a result of updating the matching pattern 51.

On the other hand, a rate for reducing a variation in ordering of the local dimension by the ordering transformation matrix 32 is obtained by causing the adjustment unit 40c to change the correspondence relations in the universal dimension matrix 32a (a testing method by changing the correspondence relations in the universal dimension).

The rate may be determines in such a way as to cause the adjustment unit 40c to increment the amount of the matching pattern 51 (by 1, for example) and to reduce a variation in ordering of the local dimension matrix 32b attributed to the change in the universal dimension matrix 32a in response to the increment (a testing method by changing the amounts in the matching pattern 51).

In this embodiment, a value calculated by summing up and averaging all the inner products obtained in accordance with the testing method by changing the amounts in matching pattern 51 and with the testing method by changing the universal dimension is used as the adjustment rate 94.

Figure 13:
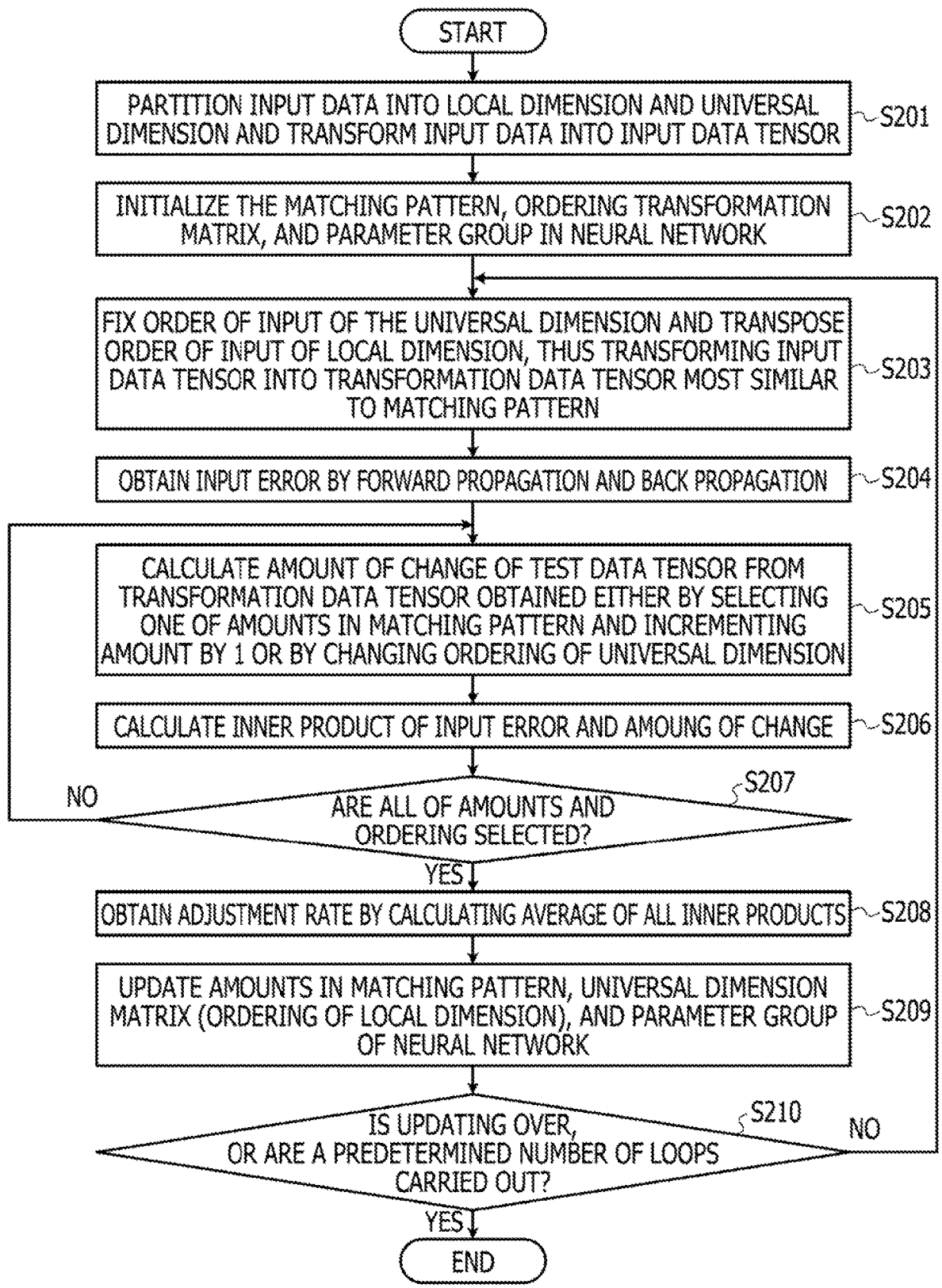
FIG. 13 is a flowchart for explaining learning processing.

FIG. 13 is a flowchart for explaining the learning processing. According to FIG. 13, the tensor creation unit 20 partitions the input data 30 into the local dimension and the universal dimension, thus transforming the input data 30 into the input data tensor 31b (step S201).

Specifically, the tensor creation unit 20 creates the dimension partitioning data 31a by partitioning the input data 30, that is, the series data 30a into the local dimension and the universal dimension. The tensor creation unit 20 obtains the input data tensor 31b by setting the amounts to the created dimension partitioning data 31a.

Steps S202 to S210 are carried out by the learning unit 40. In the learning unit 40, the initialization unit 40a initializes the matching pattern 51, the ordering transformation matrix 32, and the parameter group 71 in the neural network 41 to begin with (step S202).

The initialization unit 40a creates all the combinations of the local dimension and the universal dimension, and sets the amounts at random to the respective combinations. For example, random values in a range from −1 to 1 may be used herein. Nonetheless, the method of setting the amounts is not limited to this example. The amounts may be set in accordance with a method determined in advance by a user. As illustrated in FIG. 12, the initialization unit 40a performs association so as to achieve the transformation to the same location in the universal dimension matrix 32a, and creates the ordering transformation matrix 32 in the storage unit 130 while setting the values outside the universal dimension matrix 32a and the local dimension matrix 32b to 0. Moreover, the initialization unit 40a initializes a weight value of the parameter group 71.

Thereafter, the search unit 40b fixes the order of input of the universal dimension and transposes the order of input of the local dimension, thereby transforming the input data tensor 31b into the transformation data tensor 61 which is most similar to the matching pattern 51 (step S203).

The search unit 40b calculates an inner product of an amount vector 61v obtained by sequentially transposing the amounts in the transformation data tensor 61 and an amount vector 51v obtained by sequentially transposing the amounts in the matching pattern 51 for each transposition pattern. The search unit 40b uses the calculated inner product as the similarity of the transformation data tensor 61 to the matching pattern 51. In view of the similarities (the inner products) obtained from all the transformation data tensors 61, the search unit 40b specifies the transformation data tensor 61 having the maximum similarity.

The search unit 40b obtains the input error 64 by conducting the forward propagation and the back propagation (step S204). The search unit 40b inputs the amounts in the transformation data tensor 61 having the maximum similarity to the nodes of the neural network 41 in accordance with the order of input, thus obtaining a classification result 39 (FIG. 17) (the forward propagation). The search unit 40b calculates the output error 63 between the classification result 39 and the teaching label 33a, and obtains the input error 64 by using the calculated output error 63 and the parameter group 71 (the back propagation).

Next, the adjustment unit 40c calculates the amount of change 83 of the test data tensor 81 from the transformation data tensor 61, which is obtained either by selecting one of the amounts in the matching pattern 51 and incrementing the amount by 1, or by changing the ordering of the universal dimension (step S205).

The adjustment unit 40c selects one of the amounts in the matching pattern 51 and increments the amount by 1. Next, the adjustment unit 40c creates the test data tensors 81 depending on the order of input after transposing the correspondence relation of two elements in the local dimension matrix 32b or the universal dimension matrix 32a. Then, the adjustment unit 40c specifies a test data tensor 81 out of the created test data tensors 81, which is most similar to the matching pattern 51. The adjustment unit 40c calculates the amount of change 83 of the specified test data tensor 81 from the transformation data tensor 61. The adjustment unit 40c calculates the amounts of change 83 regarding all the amounts in the matching pattern 51 by repeating the above-mentioned processing.

When all the amounts in the matching pattern 51 are selected, the adjustment unit 40c selects two elements from the universal dimension matrix 32a and transposes the association, thus creating the test data tensor 81 with the changed order of input of the amounts. Then, the adjustment unit 40c specifies a test data tensor 81 out of the created test data tensors 81, which is most similar to the matching pattern 51. The adjustment unit 40c calculates the amount of change 83 of the specified test data tensor 81 from the transformation data tensor 61. The adjustment unit 40c calculates the amounts of change 83 regarding all the combinations of two elements in the universal dimension matrix 32a by repeating the above-mentioned processing.

The adjustment unit 40c calculates an inner product of an amount vector obtained by sequentially transposing the amounts in the test data tensor 81 and an amount vector obtained by sequentially sorting the amounts in the matching pattern 51. The adjustment unit 40c uses the calculated inner product as the similarity of the transformation data tensor 61 to the matching pattern 51. In view of the similarities (the inner products) obtained from all the transformation data tensors 61, the adjustment unit 40c may specify the transformation data tensor 61 having the maximum similarity.

Then, the adjustment unit 40c calculates the inner products 84 of the input error 64 and the obtained amounts of change 83 and stores the calculated values in the storage unit 130 (step S206). The inner products 84 thus calculated are stored one by one in the storage unit 130.

The adjustment unit 40c determines whether or not all the amounts and the ordering are selected (step S207). When the entire processing of calculating the inner products 84 depending on the respective changes in amount of the matching pattern 51 or calculating the inner products 84 depending on the respective changes in association in the universal dimension matrix 32a is not completed (NO in step S207), the adjustment unit 40c returns to step S205 and repeats the above-described processing.

On the other hand, when the entire processing of calculating the inner products 84 depending on the respective changes in amount of the matching pattern 51 or calculating the inner products 84 depending on the respective changes in association in the universal dimension matrix 32a is completed (YES in step S207), the adjustment unit 40c obtains an adjustment rate by calculating an average of all the inner products 84 (step S208), and the adjustment unit 40c terminates the adjustment processing. Next, the updating unit 40d performs update processing.

The updating unit 40d updates the amounts in the matching pattern 51, the universal dimension matrix 32a in the ordering transformation matrix 32, and the parameter group 71 in the neural network 41 (step S209). The updating unit 40d updates the respective amount in the matching pattern 51 by using at least the adjustment rate 94.

When the adjustment rate 94 (the average value of the inner products 84) is negative, the updating unit 40d determines that a direction of changes in the correspondence relations indicated by the universal dimension matrix 32a expands the input error 64 in a negative direction. On the other hand, if the adjustment rate 94 is positive, the updating unit 40d determines that the direction of changes in the correspondence relations indicated by the universal dimension matrix 32a expands the input error 64 in a positive direction. The updating unit 40d changes the correspondence relations indicated by the universal dimension matrix 32a based on the result of determination.

Moreover, the updating unit 40d updates the parameter group 71 in the neural network 41 by using at least the adjustment rate 94.

When the updating unit 40d terminates the update processing, the learning apparatus 100 determines whether the updating is over or whether a predetermined number of loops are carried out (step S210). If the updating is not over yet and the predetermined number of loops are not carried out yet (NO in step S210), the learning apparatus 100 returns to step S201 and repeats the above-described processing. On the other hand, when the updating is over or the predetermined number of loops are carried out (YES in step S210), the learning apparatus 100 terminates the entire processing.

In the above-described processing, the input data 30 targeted for learning usually includes multiple pieces of the series data 30a. Accordingly, the input data tensor 31b is created for each piece of the series data 30a. In this regard, the adjustment rate 94 becomes an average value of the inner products obtained by subjecting all the input data tensors 31b to the processing from steps S203 to S207.

Figure 14:
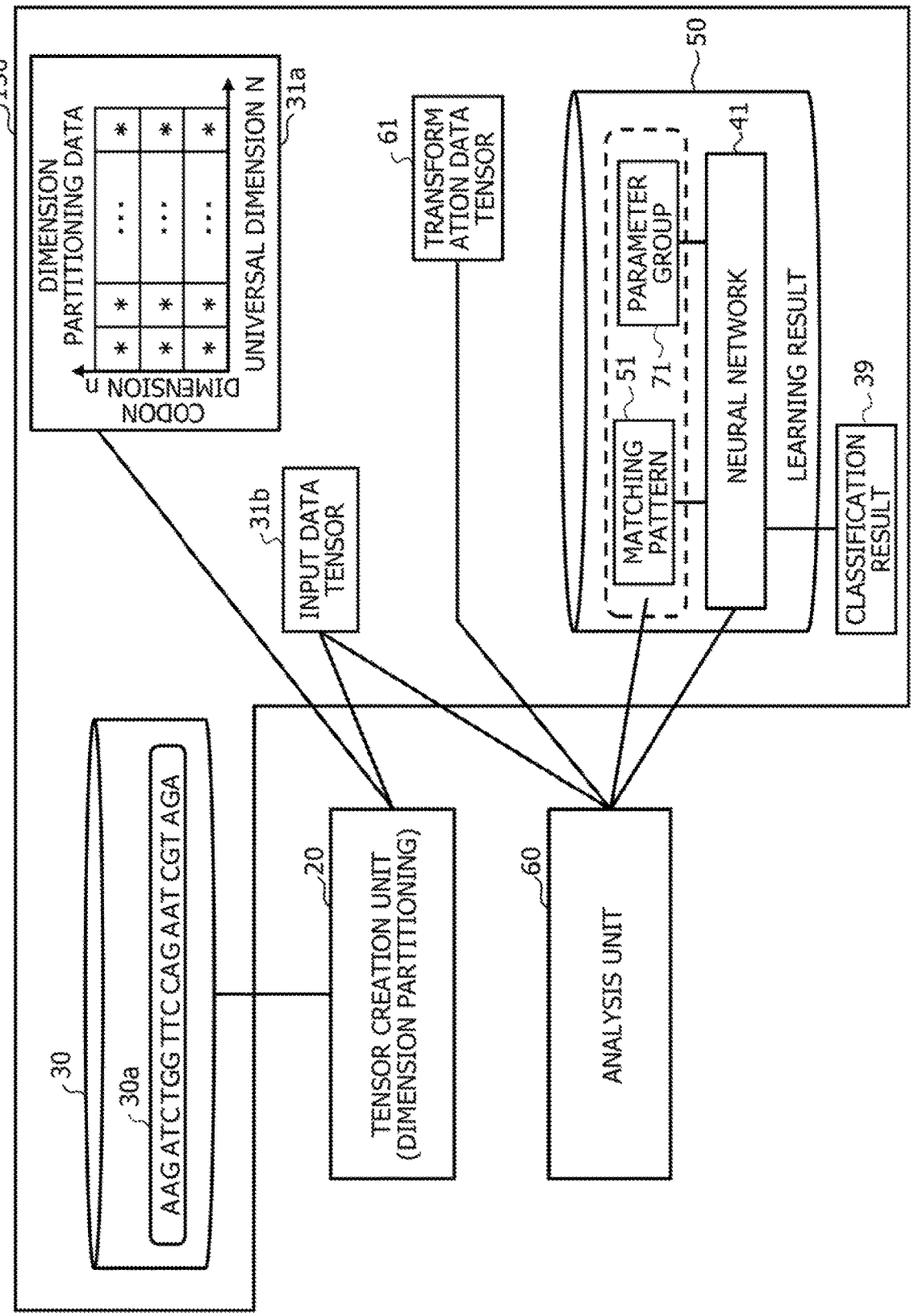
FIG. 14 is a diagram for explaining analysis processing by an analysis unit.

FIG. 14 is a diagram for explaining analysis processing by the analysis unit. According to FIG. 14, with regard to the inputted series data 30a, the tensor creation unit 20 partitions the series data 30a into the local dimension and the universal dimension as with the above-described learning processing, and the series data 30a is transformed into the input data tensor 31b by setting the amounts of bases specified in the local dimension and the universal dimension.

The analysis unit 60 changes the order of input of the input data tensor 31b and thus transforms the input data tensor 31b into the transformation data tensor 61 which is most similar to the amounts of the input order of the matching pattern 51. The analysis unit 60 inputs the amounts to the neural network 41 in accordance with the order of input based on the obtained transformation data tensor 61, thus obtaining the classification result 39.

The analysis unit 60 optimizes the order of input of the input data tensor 31b created by the tensor creation unit 20 to the neural network 41 by using the matching pattern 51 learned by the learning unit 40. Thus, it is possible to obtain the highly accurate classification result 39.

Next, a description is given of the learning processing involving the series data 30a, which is conducted by the learning unit 40 of the learning apparatus 100. Of the learning processing, search processing by the search unit 40b is described with reference to FIGS. 15 to 17 to begin with. The following explanation is made on a simple example of defining the series data 30a representing a sequence different from the aforementioned gene sequence as the input data 30 to be expressed in the format of (local dimension, universal dimension, amount) as follows:

(b1, e1, 1);
(b2, e1, 3);
(b1, e2, 2); and
(b2, e2, 0).

Note that the universal dimension matrix 32a includes the elements e1 and e2, while the local dimension matrix 32b includes the elements b1 and b2.

The matching pattern 51 is assumed to be initialized by initialization unit 40a as:

(b'1, e'1, 0.2);
(b'2, e'1, 0.1);
(b'1, e'2, −0.3); and
(b'2, e'2, 0.4).

Note that this example describes the case of randomly setting the values in the range from −1 to 1 to the respective amounts. However, the setting method is not limited to this configuration.

Figure 15:
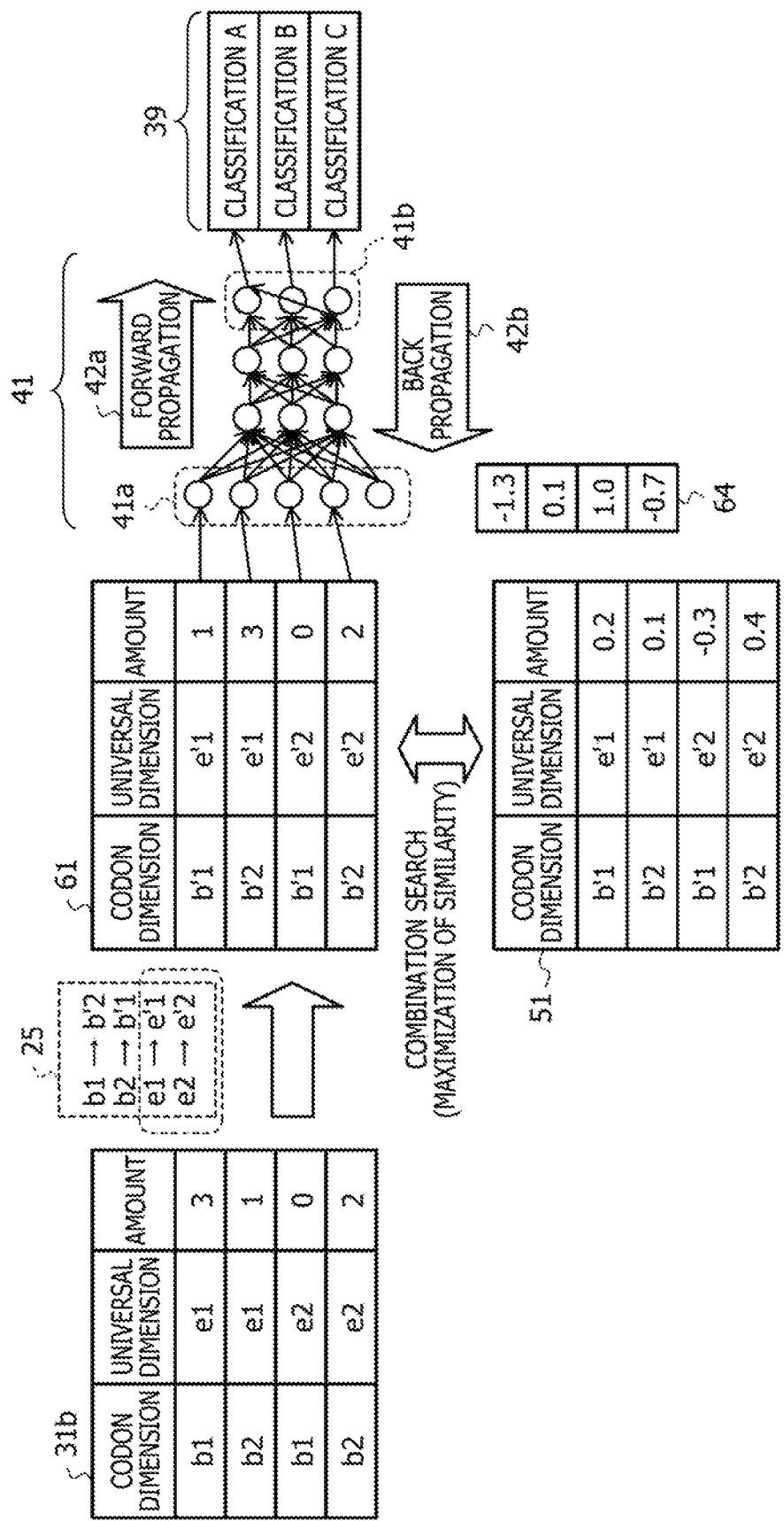
FIG. 15 is a diagram for explaining an example of search processing by a search unit.

FIG. 15 is a diagram for explaining an example of the search processing by the search unit. According to FIG. 15, the search unit 40b calculates the similarity to the matching pattern 51 for each of transposition patterns of the order of input based on the input data tensor 31b, and creates the transformation data tensor 61 based on a transposition pattern 25 having the maximum similarity out of the similarities thus obtained.

The search unit 40b sequentially inputs the amounts from the transformation data tensor 61 to an input layer 41a of the neural network 41. For example, a first amount in the transformation data tensor 61 is inputted to a first node on the input layer 41a in accordance with a predetermined order. The sample applies to a second amount in the transformation data tensor 61 and so on. In this embodiment, the order from top to bottom of the nodes on the input layer 41a is determined as the order of input.

As a consequence, a first amount "3" in the transformation data tensor 61 is inputted to a first node on the input layer 41a, a second amount "1" in the transformation data tensor 61 is inputted to a second node on the input layer 41a, a third amount "0" in the transformation data tensor 61 is inputted to a third node on the input layer 41a, and a fourth amount "2" in the transformation data tensor 61 is inputted to a fourth node on the input layer 41a.

When all the amounts are inputted onto the input layer 41*a*, the neural network 41 learns the data by forward propagation 42*a*, obtains output values at respective nodes on an output layer 41*b*, and outputs the classification result 39 by arranging the output values. The classification result 39 may indicate respective probabilities of a classification A, a classification B, and a classification C, or may indicate the highest probability only.

Moreover, the search unit 40*b* obtains the input error 64 by conducting back propagation 42*b* in the neural network 41 while using the obtained classification result 39 and the output error 63 relative to the teaching label 33*a* associated with the series data 30*a*.

Figure 16:
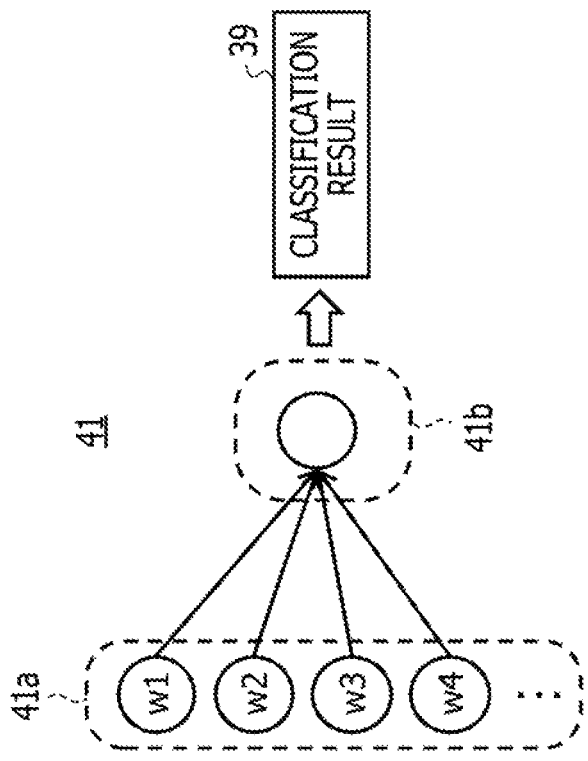
FIGS. 16A, 16B, and 16C illustrate a setting example concerning a neural network.

A description is given below concerning the neural network 41 while using a setting example as illustrated in FIG. 16.

FIG. 16 (i.e., FIGS. 16A and 16B) illustrates a setting example concerning the neural network. FIG. 16(A) depicts a simplified example of the neural network 41 illustrated in FIG. 15. The neural network 41 includes two layers, namely, the input layer 41*a* and the output layer 41*b*. The input layer 41*a* includes multiple nodes while the output layer 41*b* includes one node.

FIG. 16(B) illustrates values of parameters allocated to the respective nodes in the neural network 41. The parameters designates weight values for the respective nodes, which are indicated by w1, w2, w3, w4, and so forth. The respective weight values are initialized by the initialization unit 40*a*. FIG. 16(B) illustrates an example of setting "1.2" to w1, "0.1" to w2, "−0.9" to w3, "0.6" to w4, and so on.

FIG. 16(C) illustrates an example of correspondence relations of the classifications with the teaching labels. In FIG. 16(C), the series data 30*a* is classified into any one of the classification A, the classification B, the classification C, and so forth. A teaching label 33*a* is associated with each of the classifications. In this example, "1.0" is set to the classification A, "2.0" is set to the classification B, "3.0" is set to the classification C, and so on.

A description is given of the setting example of FIG. 16 in a case of learning so as to achieve accurate classification to the classification A while using the series data 30*a* provided with the teaching label 33*a* of the classification A included in the teaching data DB 33. The teaching label 33*a* having the value "1.0" is used herein. First, a detailed description is given of the forward propagation 42*a* and the back propagation 42*b* of FIG. 15.

Figure 17:
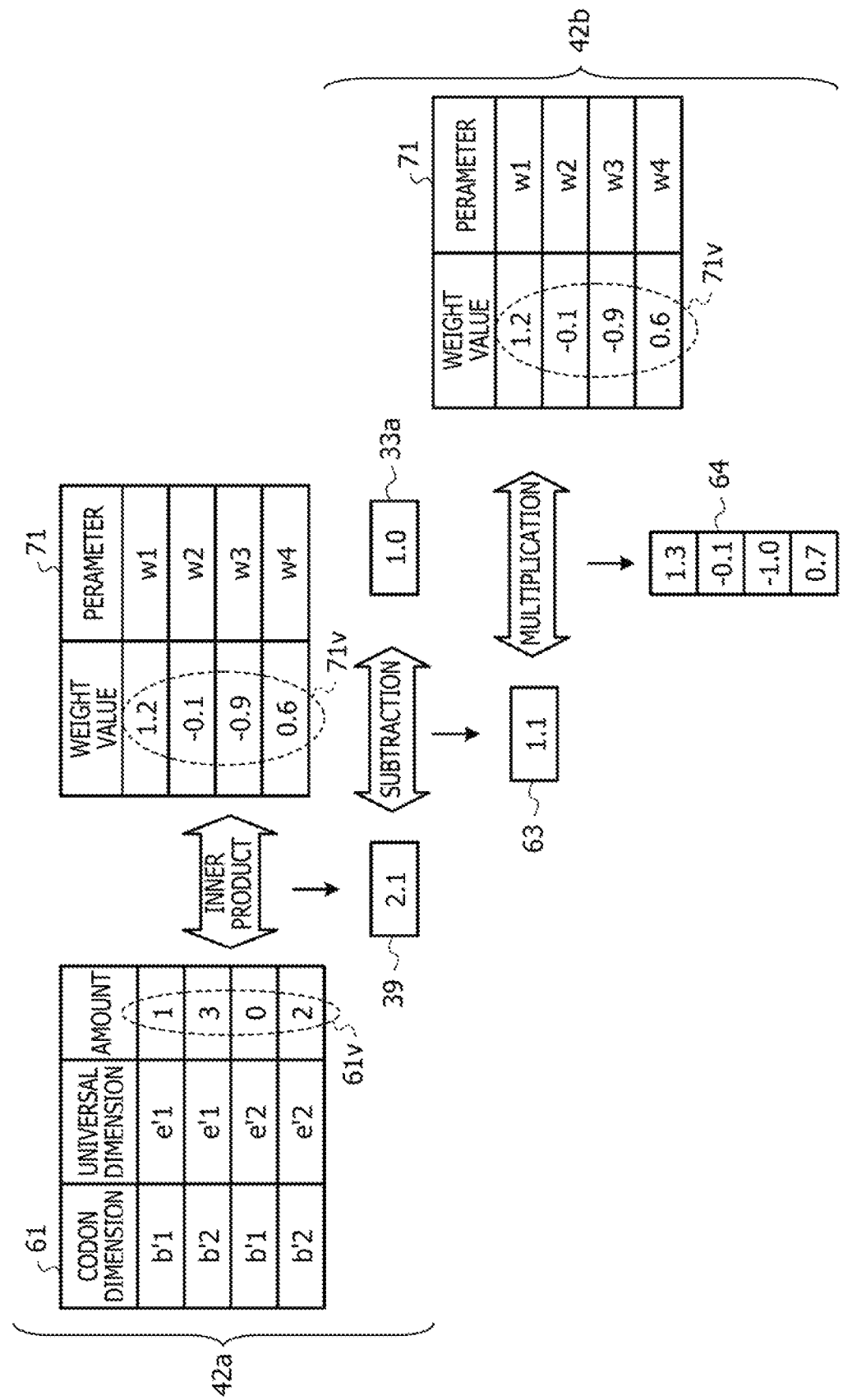
FIG. 17 is a diagram for explaining forward propagation and back propagation.

FIG. 17 is a diagram for explaining the forward propagation and the back propagation. According to FIG. 17, the classification result 39 is obtained in the forward propagation 42*a* in the neural network 41 by calculating the inner product of the amount vector 61*v* that indicates the values in the transformation data tensor 61 in the order of input and a weight vector 71*v* that indicates the weight values in the order of arrangement of the nodes in the input layer 41*a*.

In this example, the following calculations are performed, and then the inner product "2.1" is obtained by summing up results of these calculations.

1×1.2=1.2,
3×(−0.1)=−0.3,
0×(−0.9)=0, and
2×0.6=1.2.

Note that the inner product "2.1" is obtained by calculating an equation of "1.2−0.3+0+1.2", and the calculated inner product is used as the classification result 39.

Next, the back propagation 42*b* is carried out in the neural network 41 by using the classification result 39. The teaching label 33*a* of the classification A indicates "1.0". The output error 63 is obtained by subtracting the teaching label 33*a* from the classification result 39. For example, 2.1−1.0=1.1.

The input error 64 is obtained by multiplying the respective elements in the weight vector 71*v* by the output error 63. For example, 1.1×1.2, hence about 1.3,
1.1×(−0.1), hence about −0.1,
1.1×(−0.9), hence about −1.0, and
1.1×0.6, hence about 0.7 are obtained, whereby the input error 64 turns out to be (1.3, −0.1, −1.0, 0.7).

Next, adjustment processing by the adjustment unit 40*c* is described with reference to FIGS. 18 to 22. First, a testing method by changing the amounts in the matching pattern 51 is described with reference to FIGS. 18 to 21 as processing for obtaining the adjustment rate 94.

Figure 18:
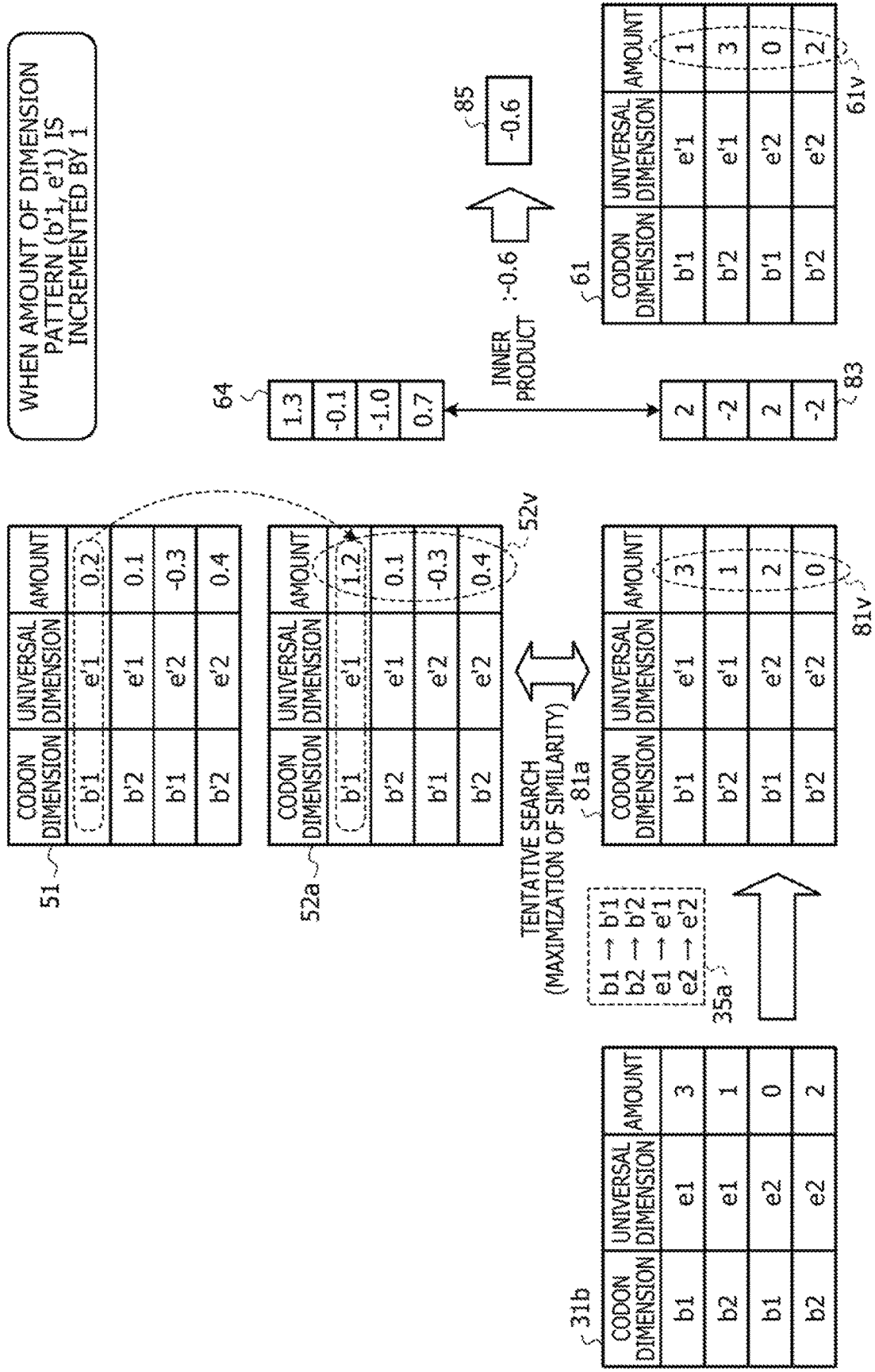
FIG. 18 is a first diagram for explaining a testing method by changing amounts in matching patterns.

FIG. 18 is a first diagram for explaining the testing method by changing the amounts the in matching patterns. The adjustment unit 40*c* conducts a test by incrementing the records in the matching pattern 51 by 1 sequentially from the first record. FIG. 18 describes a processing example in the case where the amount of the dimension pattern (b'1, e'1) indicated in the first record in the matching pattern 51 is incremented by 1.

A matching pattern 52*a* is created by incrementing the amount of the dimension pattern (b'1, e'1) by 1 and the amount of the first record in the matching pattern 52*a* turns out to be "1.2". Regarding the input data tensor 31*b*, the adjustment unit 40*c* conducts a tentative search to search a test data tensor 81*a* most similar to the matching pattern 52*a* while transposing the correspondence relations between two elements in either the universal dimension matrix 32*a* or the local dimension matrix 32*b*.

In the tentative search, the adjustment unit 40*c* creates a test data tensor 81*a* by selecting two elements in the universal dimension matrix 32*a* or two elements in the local dimension matrix 32*b*. The adjustment unit 40*c* calculates an inner product (a similarity) of an amount vector 81*v* that indicates an amount of the created test data tensor 81*a* as an element and an amount vector 52*v* that indicates am amount of the matching pattern 52*a* as an element.

When the transposition of all the correspondence relations is completed, the adjustment unit 40*c* specifies the test data tensor 81*a* having the largest value out of the inner products calculated depending on each transposition. Specifically, the test data tensor 81*a* that is most similar to the matching pattern 52*a* is determined from the test data tensors 81*a* created depending on the selections of the two elements. In this example, the test data tensor 81*a* for a transposition pattern 35*a* in the universal dimension matrix 32*a* is most similar to the matching pattern 52*a*.

The adjustment unit 40*c* calculates the amount of change 83 between the test data tensor 81*a* most similar to the matching pattern 52*a* and the transformation data tensor 61 created by the search unit 40*b*. Specifically, the amount of change 83 is obtained by calculating a difference between the amount vector 81*v* of the test data tensor 81*a* and the amount vector 61*v* of the transformation data tensor 61. In this example, 3−1=2 is obtained by a subtraction between two first elements,
1−3=−2 is obtained by a subtraction between two second elements,
2−0=2 is obtained by a subtraction between two third elements, and
0−2=−2 is obtained by a subtraction between two fourth elements.

Accordingly, the amount of change 83 turns out to be (2, −2, 2, −2).

Next, the adjustment unit 40c calculates the inner product between the input error 64 calculated by the search unit 40b and the amount of change 83. In this example, an equation of "1.3×2+(−0.1)×(−2)+(−1.0)×2+0.7×(−2)" is calculated, and then a value "−0.6", is obtained as a calculation result. The adjustment unit 40c accumulates the value "−0.6", which indicates an impact of the change in amount of the dimension pattern (b'1, e'1) on the ordering of the local dimension, in inner product data 85.

Figure 19:
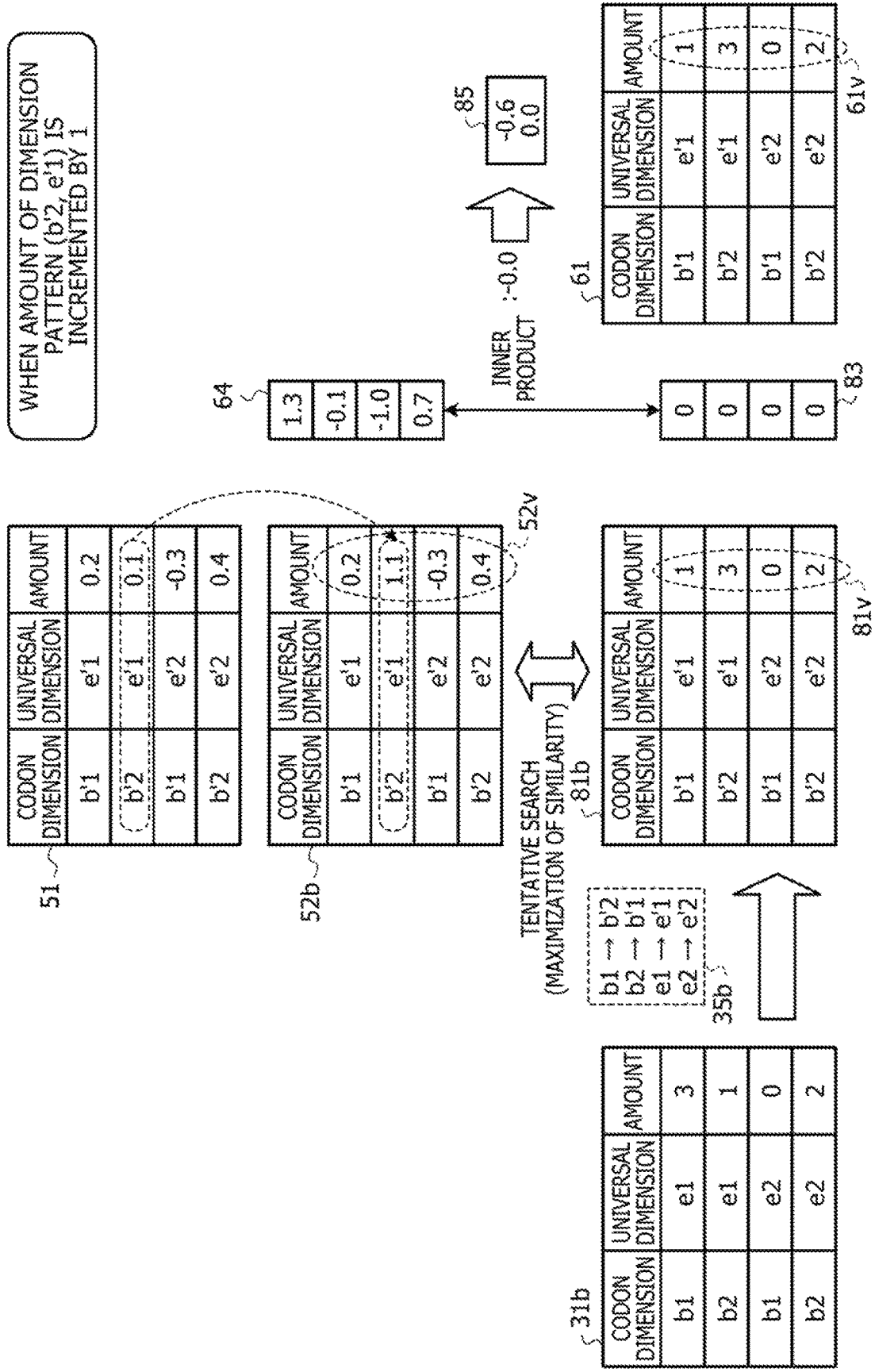
FIG. 19 is a second diagram for explaining the testing method by changing the amounts in the matching patterns.

FIG. 19 is a second diagram for explaining the testing method by changing the amounts in the matching patterns. FIG. 19 describes a processing example in the case where the amount of the dimension pattern (b'2, e'1) indicated in the second record in the matching pattern 51 is incremented by 1.

A matching pattern 52b is created by incrementing the amount of the dimension pattern (b'2, e'1) by 1 and the amount of the second record in the matching pattern 52b turns out to be "1.1". Regarding the input data tensor 31b, the adjustment unit 40c conducts a tentative search to search a test data tensor 81b most similar to the matching pattern 52b. This tentative search is similar to the tentative search in FIG. 18 and a detailed description thereof is omitted.

In this example, the test data tensor 81b most similar to the matching pattern 52b is specified in the case of a transposition pattern 35b. The adjustment unit 40c calculates the amount of change 83 between the test data tensor 81b most similar to the matching pattern 52b and the transformation data tensor 61 created by the search unit 40b. Regarding the amount vector 81v of the test data tensor 81b and the amount vector 61v of the transformation data tensor 61, 1−1=0 is obtained by a subtraction between two first elements, 3−3=0 is obtained by a subtraction between two second elements, 0−0=0 is obtained by a subtraction between two third elements, and 2−2=0 is obtained by a subtraction between two fourth elements.

Accordingly, the amount of change 83 turns out to be (0, 0, 0, 0).

Next, the adjustment unit 40c calculates the inner product between the input error 64 calculated by the search unit 40b and the amount of change 83. In this example, 1.3×0+(−0.1)×0+(−1.0)×0+0.7×0=0.0 is obtained. The adjustment unit 40c accumulates the value "0.0", which indicates an impact of the change in amount of the dimension pattern (b'2, e'1) on the ordering of the local dimension, in the inner product data 85.

Figure 20:
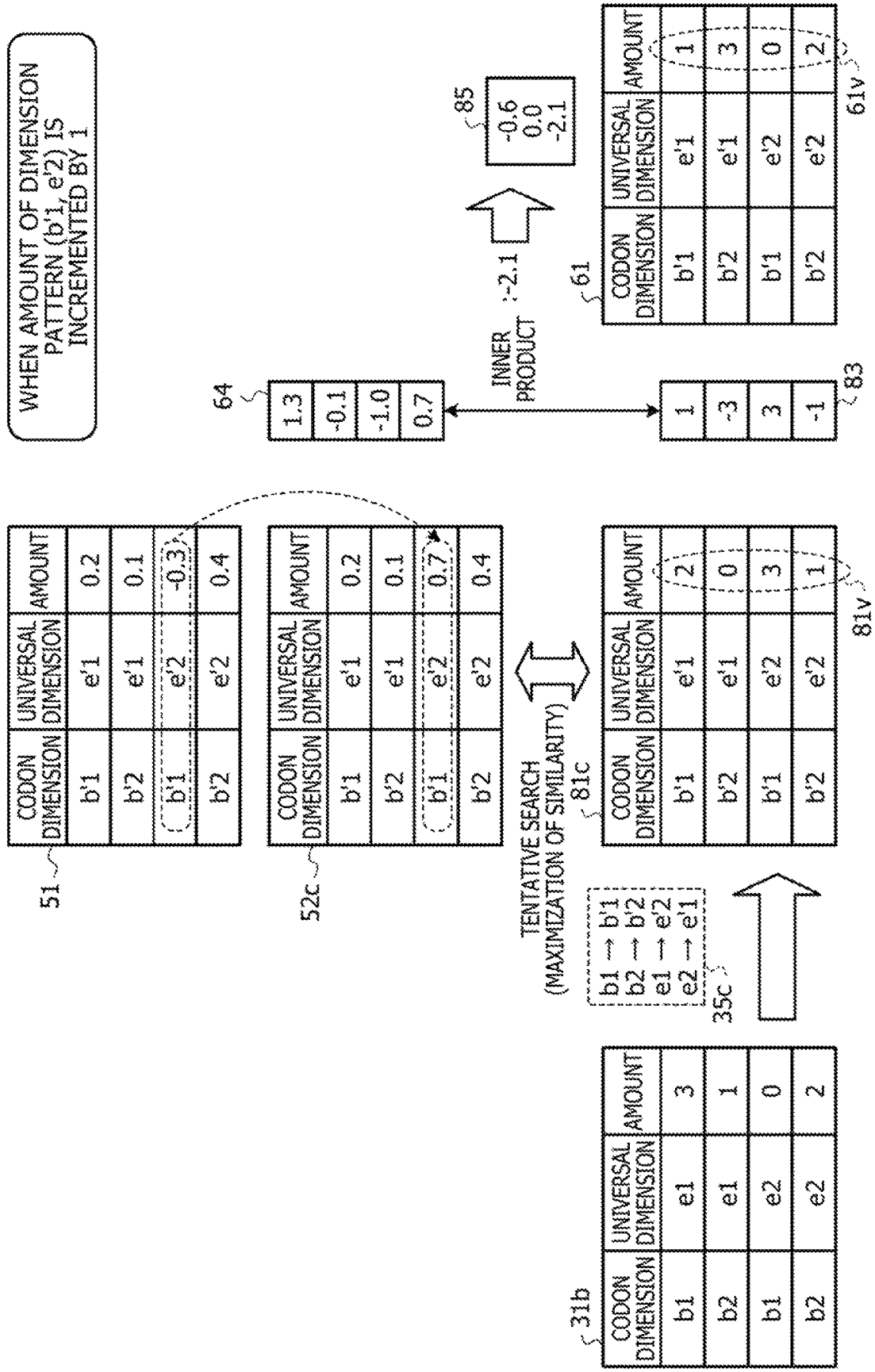
FIG. 20 is a third diagram for explaining the testing method by changing the amounts in the matching patterns.

FIG. 20 is a third diagram for explaining the testing method by changing the amounts in the matching patterns. FIG. 20 describes a processing example in the case where the amount of the dimension pattern (b'1, e'2) indicated in the third record in the matching pattern 51 is incremented by 1.

A matching pattern 52c is created by incrementing the amount of the dimension pattern (b'1, e'2) by 1 and the amount of the third record in the matching pattern 52c turns out to be "0.7". Regarding the input data tensor 31b, the adjustment unit 40c conducts a tentative search to search a test data tensor 81c most similar to the matching pattern 52c. This tentative search is similar to the tentative search in FIG. 18 and a detailed description thereof is omitted.

In this example, the test data tensor 81c most similar to the matching pattern 52c is specified in the case of a transposition pattern 35c. The adjustment unit 40c calculates the amount of change 83 between the test data tensor 81c most similar to the matching pattern 52c and the transformation data tensor 61 created by the search unit 40b. Regarding the amount vector 81v of the test data tensor 81c and the amount vector 61v of the transformation data tensor 61, 2−1=1 is obtained by a subtraction between two first elements, 0−3=−3 is obtained by a subtraction between two second elements, 3−0=3 is obtained by a subtraction between two third elements, and 1−2=−1 is obtained by a subtraction between two fourth elements.

Accordingly, the amount of change 83 turns out to be (1, −3, 3, −1).

Next, the adjustment unit 40c calculates the inner product between the input error 64 calculated by the search unit 40b and the amount of change 83. In this example, 1.3×1+(−0.1)×(−3)+(−1.0)×3+0.7×(−1)=−2.1 is obtained. The adjustment unit 40c accumulates the value "−2.1", which indicates an impact of the change in amount of the dimension pattern (b'1, e'2) on the ordering of the local dimension, in the inner product data 85.

Figure 21:
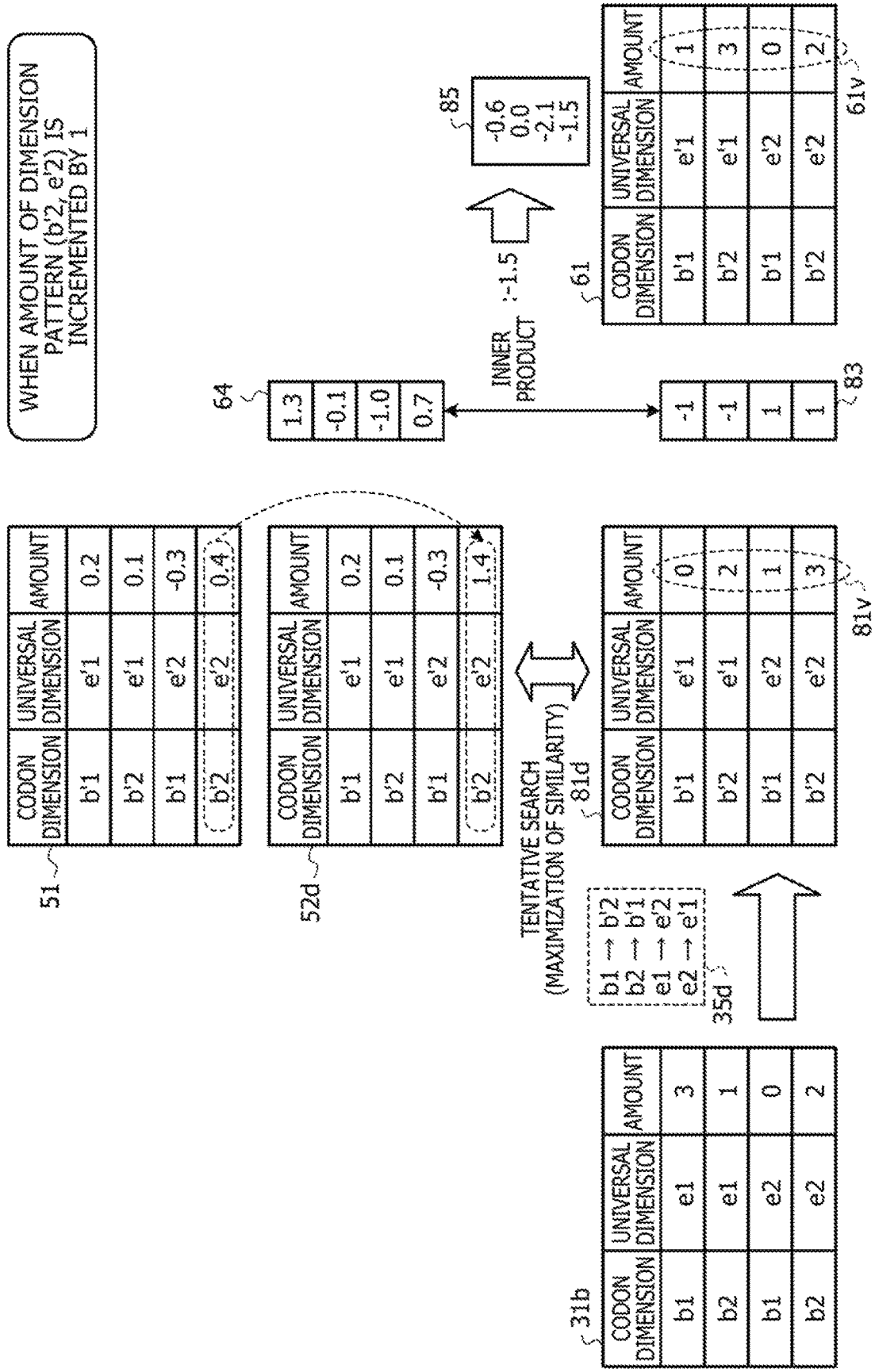
FIG. 21 is a fourth diagram for explaining the testing method by changing the amounts in the matching patterns.

FIG. 21 is a fourth diagram for explaining the testing method by changing the amounts in the matching patterns. FIG. 21 describes a processing example in the case where the amount of the dimension pattern (b'2, e'2) indicated in the fourth record in the matching pattern 51 is incremented by 1.

A matching pattern 52d is created by incrementing the amount of the dimension pattern (b'2, e'2) by 1 and the amount of the fourth record in the matching pattern 52d turns out to be "1.4". Regarding the input data tensor 31b, the adjustment unit 40c conducts a tentative search to search a test data tensor 81d most similar to the matching pattern 52d. This tentative search is similar to the tentative search in FIG. 18 and a detailed description thereof is omitted.

In this example, the test data tensor 81d most similar to the matching pattern 52d is specified in the case of a transposition pattern 35d. The adjustment unit 40c calculates the amount of change 83 between the test data tensor 81d most similar to the matching pattern 52d and the transformation data tensor 61 created by the search unit 40b. Regarding the amount vector 81v of the test data tensor 81d and the amount vector 61v of the transformation data tensor 61, 0−1=−1 is obtained by a subtraction between two first elements, 2−3=−1 is obtained by a subtraction between two second elements, 1−0=1 is obtained by a subtraction between two third elements, and 3−2=1 is obtained by a subtraction between two fourth elements.

Accordingly, the amount of change 83 turns out to be (−1, −1, 1, 1).

Next, the adjustment unit 40c calculates the inner product between the input error 64 calculated by the search unit 40b and the amount of change 83. In this example, 1.3×(−1)+(−0.1)×(−1)+(−1.0)×1+0.7×1=−1.5 is obtained. The adjustment unit 40c accumulates the value "−1.5", which indicates an impact of the change in amount of the dimension pattern (b'2, e'2) on the ordering of the local dimension, in the inner product data 85.

Figure 22:
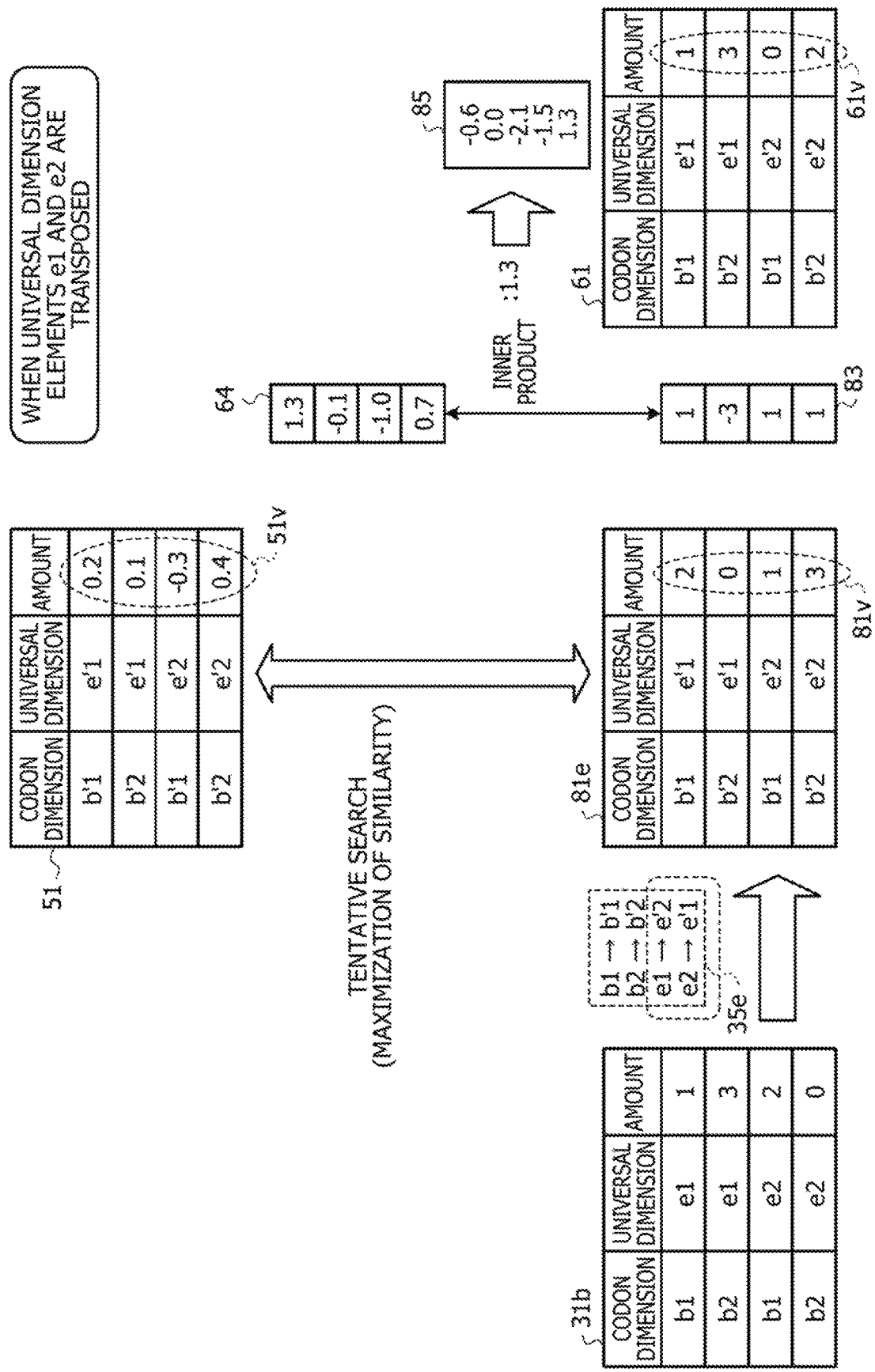
FIG. 22 is a diagram for explaining a testing method by changing correspondence relations in a universal dimension.

Next, a testing method by changing correspondence relations in the universal dimension is described with reference to FIG. 22. FIG. 22 is a diagram for explaining a testing method by changing correspondence relations in the universal dimension. FIG. 22 describes a processing example in the case of changing the correspondence relation in the universal dimension matrix 32a in the matching pattern 51.

The association of the elements in the universal dimension matrix 32a is fixed in the processing by the search unit 40b. On the other hand, the adjustment unit 40c creates test data tensor 81e for each transposition pattern formed by transposing the association of the element of the local dimension relative to the association prepared by selecting and transposing two elements from the universal dimension.

The adjustment unit 40c selects the test data tensor 81e most similar to the matching pattern 51 out of the test data tensors 81e thus created, then calculates the amount of change 83 from the transformation data tensor 61, then obtains an inner product of the amount of change 83 and the input error 64, and adds the inner product to the inner product data 85.

In this example, the universal dimension matrix 32a consists of the two elements e1 and e2. Accordingly, the adjustment unit 40c creates the test data tensor 81e for each transposition of two elements of the local dimension in the case of transposing element e1 and the element e2.

This testing method also uses an inner product as the similarity. To be more precise, the adjustment unit 40c calculates an inner product of the amount vector 51v obtained by sequentially arranging the amounts in the matching pattern 51 and the amount vector 81v obtained by sequentially arranging the amounts in the test data tensor 81e. The adjustment unit 40c specifies the test data tensor 81e most similar to the matching pattern 51.

In this example, the test data tensor 81e most similar to the matching pattern 51 is specified in the case of a transposition pattern 35e. The adjustment unit 40c calculates the amount of change 83 between the test data tensor 81e most similar to the matching pattern 51 and the transformation data tensor 61 created by the search unit 40b. Regarding the amount vector 81v of the test data tensor 81e and the amount vector 61v of the transformation data tensor 61, 2−1=1 is obtained by a subtraction between two first elements, 0−3=−3 is obtained by a subtraction between two second elements, 1−0=1 is obtained by a subtraction between two third elements, and 3−2=1 is obtained by a subtraction between two fourth elements.

Accordingly, the amount of change 83 turns out to be (1, −3, 1, 1).

Next, the adjustment unit 40c calculates the inner product between the input error 64 calculated by the search unit 40b and the amount of change 83. In this example, 1.3×1+(−0.1)×(−3)+(−1.0)×1+0.7×1=1.3 is obtained. The adjustment unit 40c accumulates the value "1.3", which indicates an impact of the change in correspondence relation of the universal dimension on the ordering of the local dimension, in the inner product data 85.

There is just one combination of the two elements of the universal dimension in this example. However, if there are three elements, then values indicating respective update directions of six combinations are calculated and accumulated in the inner product data 85. The same applies to a case where there are four or more elements.

Figure 23:
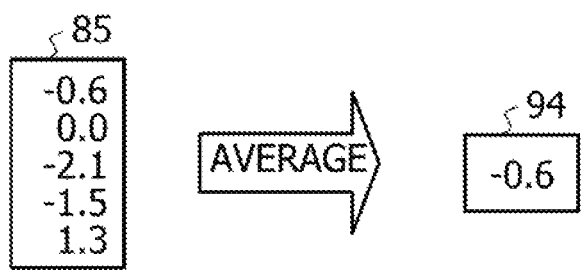
FIG. 23 is a diagram for explaining an example of calculation of an adjustment rate by an adjustment unit.

FIG. 23 is a diagram for explaining an example of calculation of an adjustment rate by the adjustment unit. According to FIG. 23, the adjustment unit 40c sums up the values accumulated in the inner product data 85 and calculates an average value thereof.

For example, based on the inner product data 85, (−0.6)+0.0+(−2.1)+(−1.5)+1.3=−2.9 is obtained and, the average value "−0.6" is hence obtained by (−2.9)/5=−0.6. The value "−0.6" indicates the magnitude and the direction of expansion of the input error 64 by the change in the ordering of the local dimension. This value is stored as the adjustment rate 94 in the storage unit 130.

Figure 24:
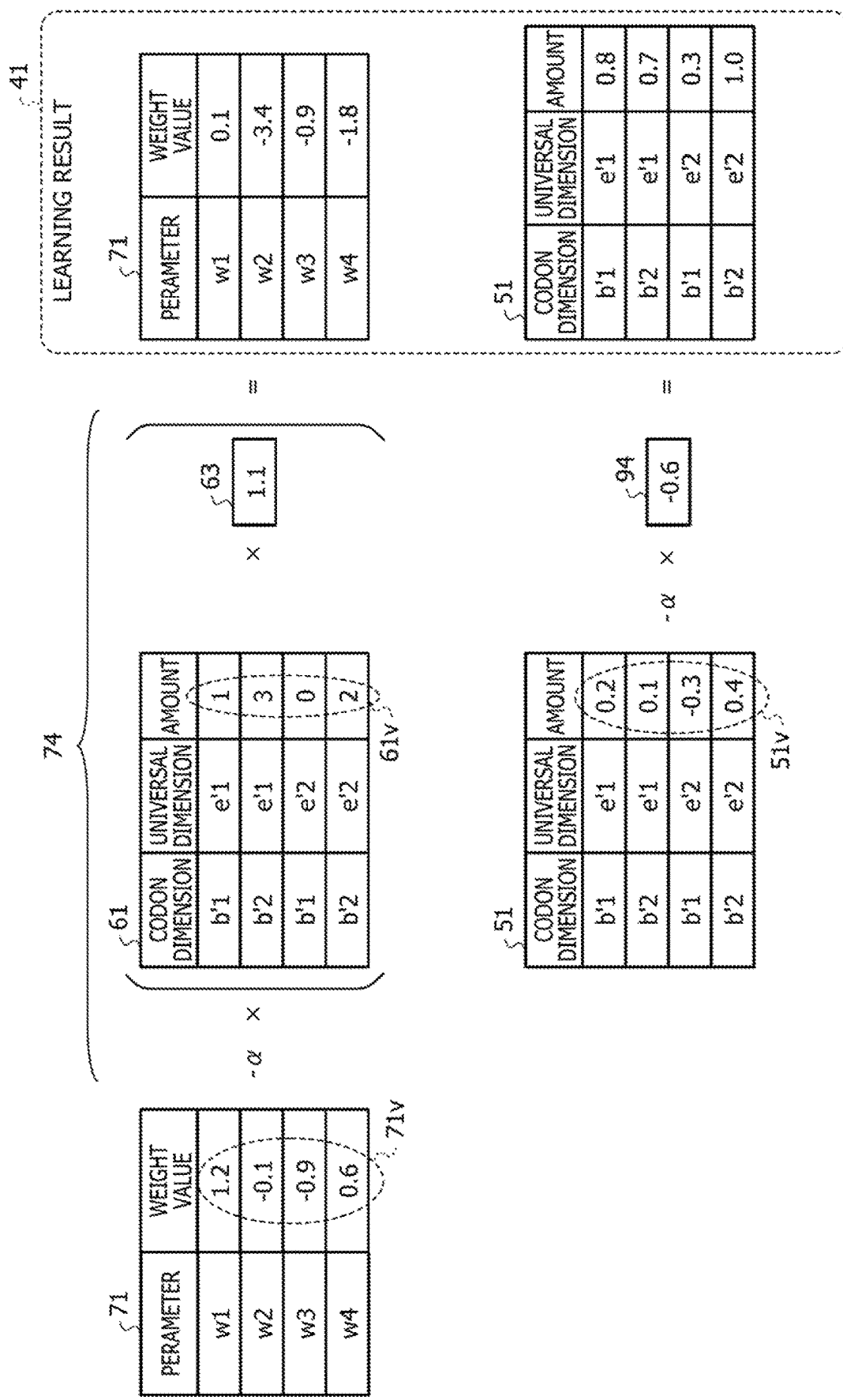
FIG. 24 illustrates an example of update processing by an updating unit.

FIG. 24 illustrates an example of update processing by the updating unit. According to FIG. 24, the updating unit 40d updates the parameter group 71 and the matching pattern 51 while taking into account the number of steps a in the neural network 41. The number steps represents the number of propagation from a tier to another tier. In the example of FIG. 16(A), the number of steps a is equal to 1.

The updating unit 40d multiplies the values of the respective elements in the amount vector 61v obtained from the transformation data tensor 61 by the output error 63 and then multiples the respective multiplied elements by the number of steps a, thereby obtaining correction values 74 used to optimize the parameter group 71. Thereafter, the updating unit 40d updates the parameter group 71 by subtracting the correction values 74 from the weight vector 71v obtained from the parameter group 71.

To be more precise, 1.2−1.1=0.1 is obtained by a subtraction between two first elements, −0.1−3.3=−3.4 is obtained by a subtraction between two second elements, −0.9−0.0=−0.9 is obtained by a subtraction between two third elements, and 0.6−2.2=−1.8 is obtained by a subtraction between two fourth elements.

Accordingly, the weight vector 71v is updated with (0.1, −3.4, −0.9, −1.8).

The updating unit 40d updates the matching pattern 51 by subtracting the adjustment rate 94 multiplied by the number of steps a from the values of the respective elements in the amount vector 51v obtained from the matching pattern 51.

To be more precise, assuming that the number of steps a is set to 1, 0.2−(1×(−0.6))=0.8 is obtained by a subtraction from the first element, 0.1−(1×(−0.6))=0.7 is obtained by a subtraction from the second element, −0.3−(1×(−0.6))=0.3 is obtained by a subtraction from the third element, and 0.4−(1×(−0.6))=1.0 is obtained by a subtraction from the fourth element.

Accordingly, the amount vector 51v is updated with (0.8, 0.7, 0.3, 1.0).

Figure 25:
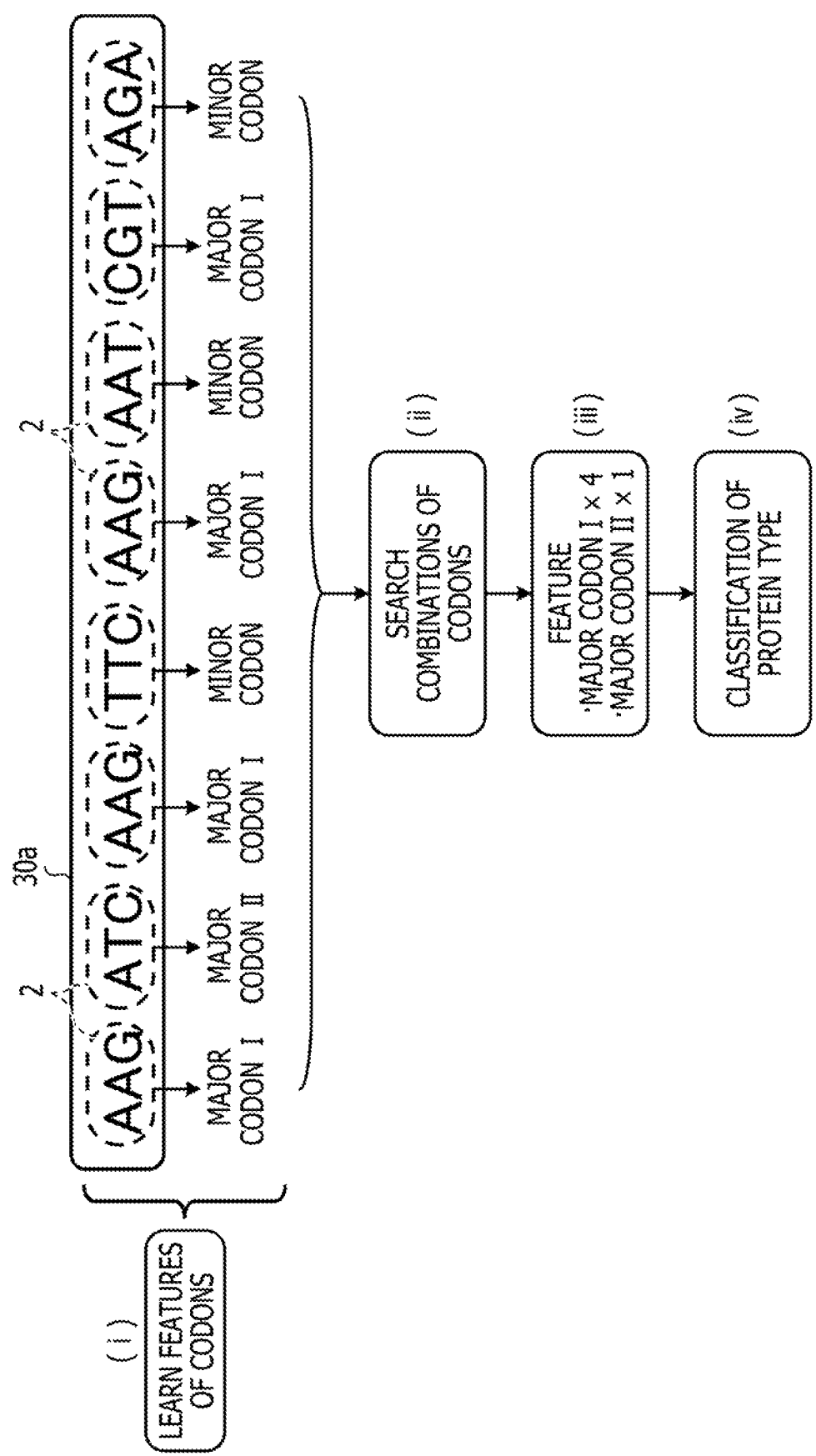
FIG. 25 is a diagram for explaining contents of learning from the series data to be achieved by the learning apparatus.

FIG. 25 is a diagram for explaining contents of learning from the series data to be achieved by the learning apparatus. According to FIG. 25, the learning apparatus 100 partitions the series data 30a representing the gene sequence into the local dimension and the universal dimension, thereby learning the features of arrangement of the bases in the respective codons 2 in terms of the local dimension (i), and learning the features obtained by combinations of the features of the codons 2 in terms of the universal dimension (ii).

As the features of the series data 30a, the learning apparatus 100 specifies:

four major codons I; and one major codon II (iii), and classifies the type of the protein at high accuracy (iv).

As a consequence of the learning, the learning apparatus 100 is capable of distinguishing two types of codons 2 as the major codons I, namely, "AAG" that appears three times and "CGT" that appears once in the series data 30*a*, and of distinguishing "ATC" that appears once therein as the major codon II classification of protein type. Meanwhile, "TTC", "AAT", and "AGA" are distinguished as minor codons. Each of "TTC", "AAT", and "AGA" appears once.

The learning apparatus 100 of this embodiment learns the order of input to the neural network 41 so as to optimize the classification accuracy, that is, the matching pattern 51 from the series data 30*a* to be characterized by the combinations of multiple local features. In other words, according to this embodiment, the learning apparatus 100 acquires a capability of distinguishing the major codons that are important for classifying the types of proteins. When this embodiment is adopted to the machine learning, it is possible to achieve the accuracy of about 0.96 or above in the classification of types of proteins based on gene sequences.

The description is made above on the premise that the input data 30 is the series data 30*a*. However, even in a case where the input data 30 is a scrambled image, it is also possible to improve classification accuracy by applying the above-described embodiment A processing example in the case of a scrambled image is going to be described. In the following processing example, the functional configuration example of the learning apparatus 100 is the same as the above description with reference to FIGS. 6, 9 to 11, and 14.

Figure 26B:
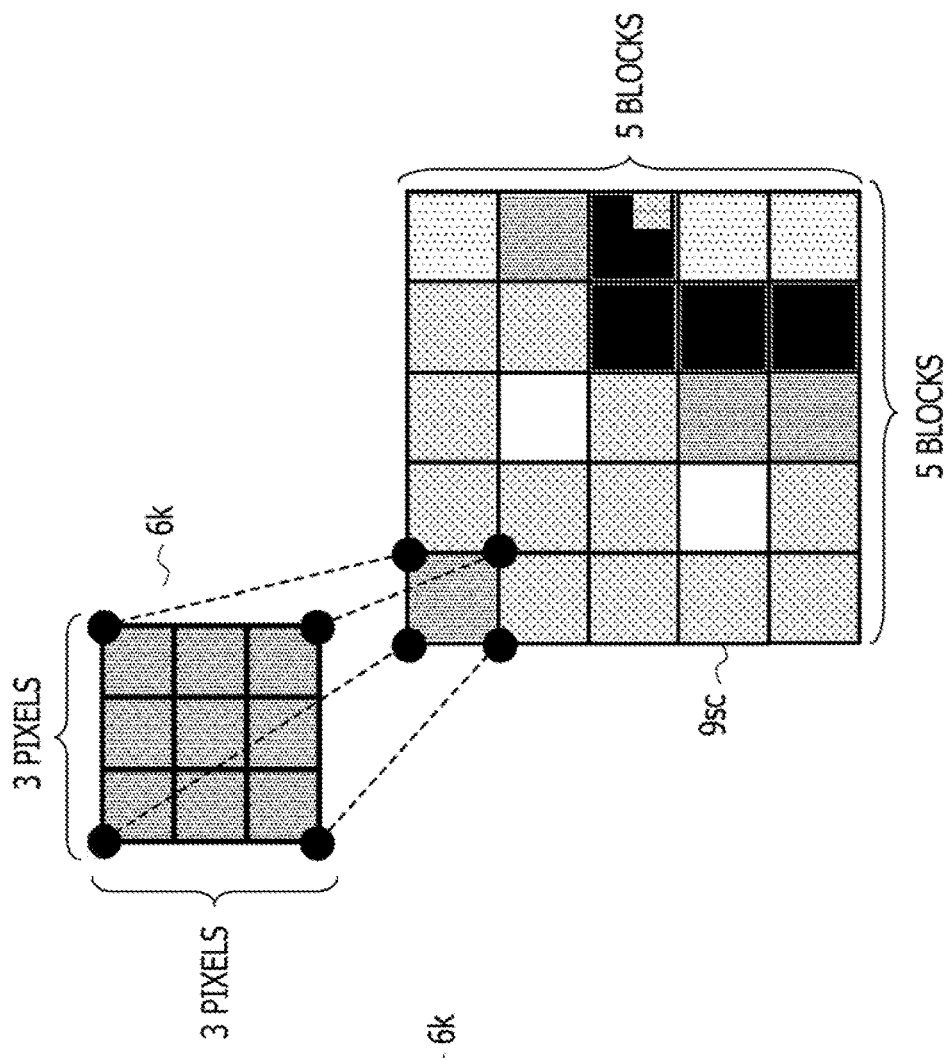
FIGS. 26A and 26B illustrate an example of a scrambled image.
Figure 26A:
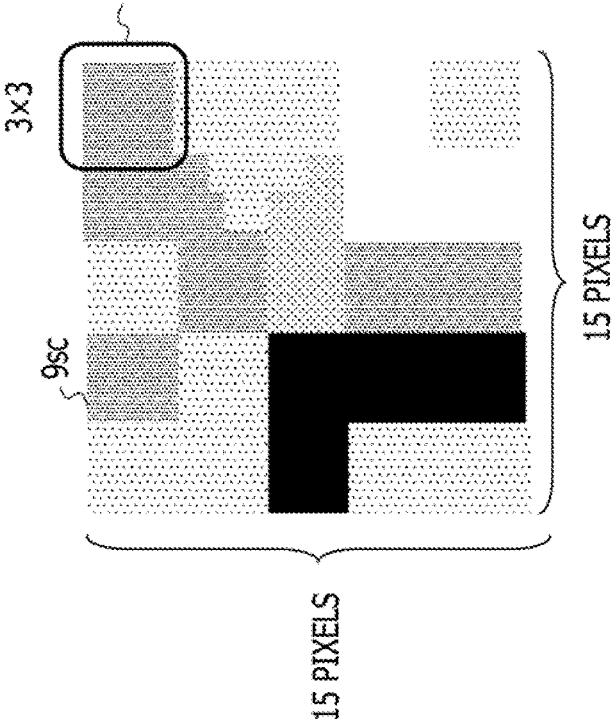

First, a scrambled image is described. FIG. 26 (i.e., FIGS. 26A and 26B) illustrates an example of a scrambled image. A scrambled image 9*sc* Illustrated in FIG. 26A represents an example of an image having a 15×15 pixel size in which 3×3 pixels are scrambled with one block 6*k*. The block 6*k* may be determined based on the image size and it not limited to 3×3 pixels. The size of one block 6*k* constitutes a local unit for creating the local dimension matrix 32*b*.

According to FIG. 26B, the pixels in each block 6*k* Indicate part of an original image and presents the part continuously by using the order of arrangement of three pixels. As a consequence, the order of arrangement has a feature. Outside each block 6*k*, a feature of the original image emerges by using a combination of adjacent blocks 6*k*.

Here, an example of a method of creating the scrambled image 9*sc* is described. FIG. 27 (i.e., FIGS. 27A, 27B, and 27C) is diagram for explaining a method of creating the scrambled image. According to FIG. 27A, an original image 9*or* is partitioned into the blocks 6*k* each containing a predetermined number of pixels. In order to facilitate the understanding, a particular color is allocated to each row (the same color in the horizontal direction) and a particular number is allocated to each column (the same number in the vertical direction).

An image 9*p* illustrated in FIG. 27B represents a result of scrambling the horizontal axis of the original image 9*or*. The order of numbers of the blocks 6*k* is scrambled. When the vertical axis is further scrambled, the order of colors of the block 6*k* is scrambled and the scrambled image 9*sc* is obtained as illustrated in FIG. 27C. In the scrambled image 9*sc* illustrated in FIG. 27C, the same numbers are vertically arranged in light of a column 9*c* and the same colors are arranged in light of a row 9*r*.

There may be a case where it is possible to identify part of an object in the scrambled image 9*sc* as a feature of an intra-block dimension such as recognition of an eye and recognition of a mouth. As a feature of an extra-block dimension, it is possible to extract a universal feature of the original image 9*or* such as recognition of a hear, a vertically elongate image, and a bluish image as a consequence of combining two certain blocks 6*k*.

Based on the above-mentioned concepts, the classification accuracy is improved by adopting the intra-block dimension to the above-mentioned local dimension and adopting the extra-block dimension to the above-mentioned universal dimension.

FIG. 28 is a diagram for explaining dimension partitioning of the scrambled image. In FIG. 28, both an intra-block dimension 7*b* and an extra-block dimension 7*a* of the scrambled image 9*sc* are expressed two-dimensionally.

A rearrangement matrix 8*b* of the elements of the intra-block dimension 7*b* is expressed by using $U_x$ and $U_y$ and the order of input is determined by the learning with the back propagation. A rearrangement matrix 8*a* of the elements of the extra-block dimension 7*a* may be expressed by using $U_X$ and $U_Y$ and the transformation data tensor 61 may be obtained in such a way as to be most similar to the matching pattern 51.

FIG. 29 (i.e., FIGS. 29A, 29B, and 29C) Illustrates a comparative example of classification accuracy. FIG. 29A illustrates an example of transforming an image 91*or* selected from a Fashion MNIST data set into a scrambled image 91*sc*. FIG. 29B illustrates an example of transforming an image 92*or* selected from a data set of CMU Faces Images into a scrambled image 92*sc*.

Using the scrambled image 91*sc* in FIG. 29A and the scrambled image 92*sc* in FIG. 29B as targets for comparison with this embodiment, the classification accuracy is compared by using a convolutional neural network (CNN) with an adjusted stride width (hereinafter referred to as comparative technique 1) and histogram formation and a support vector machine (SVM) (hereinafter referred to as comparative technique 2). Results are indicated in FIG. 29C.

As indicated in FIG. 29C, the classification accuracy of the scrambled image 91*sc* in FIG. 29A turns out to be "0.725" according to this embodiment, "0.651" according to the comparative example 1, and "0.595" according to the comparative example 2. The classification accuracy of the scrambled image 92*sc* in FIG. 29B turns out to be "0.818" according to this embodiment, "0.560" according to the comparative example 1, and "0.309" according to the comparative example 2.

From these results, the embodiment that optimizes the order of input to the neural network 41 by using the input data tensor 31*b* created by partitioning the input data 30 into the local dimension and the universal dimension seems to improve the classification accuracy of the machine learning in each of the examples.

The learning apparatus 100 of the above-described embodiment may also be used in a network system. FIG. 30 illustrates an example of a network system. In a network system 1000 illustrated in FIG. 30, multiple terminals 5 may be coupled to the learning apparatus 100 through a network int.

In the network system 1000, the learning apparatus 100 includes a hardware configuration illustrated in FIG. 5. Each terminal 5 is an information processing apparatus including a CPU 501, a primary storage device 502, an auxiliary storage device 503, an input device 504, a display device 505, a communication I/F 507, and a drive device 508, which are coupled to a bus B2. The auxiliary storage device 503, the input device 504, and an external storage device to which the terminals 5 are accessible are collectively referred to as a storage unit 530.

The CPU 501 corresponds to a processor that controls the terminals 5 and implements various kinds of processing according to this embodiment described below by executing programs stored in the storage unit 530. The input device 504 is operated by a user and inputs data in response to the operation, and the display device 505 serves as a user interface and displays various screens. The input device 504 and the display device 505 may be integrated into a touch panel. The communication I/F 507 controls communication with an external device.

The program according to this embodiment stored in a storage medium 509 (for example, a compact disc read-only memory (CD-ROM)) may be installed on the storage unit 530 via a drive device 508 to be executed by the CPU 501.

The storage medium 509 for storing the program according to this embodiment is not limited to the CD-ROM, and it may be any one or more non-transitory and tangible media having a computer-readable structure. As a computer-readable storage medium, in addition to the CD-ROM, a digital versatile disk (DVD), a portable recording medium such as a Universal Serial Bus (USB) memory, and a semiconductor memory such as a flash memory may be used.

As described above, according to this embodiment, the series data 30a is expressed by a single input data tensor 31b prepared by partitioning the series data 30a into the local dimension and the universal dimension, and the classification accuracy is improved by simultaneously learning the features of the order of arrangement of the element in the local dimension and the features of the order of arrangement of the elements in the universal dimension.

The disclosure is not limited to the specifically disclosed embodiment, and various modifications and variations are possible without departing from the scope of the claims.

The tensor creation unit 20 described in the embodiment represents an example of a creation unit while the search unit 40b and the adjustment unit 40c in the learning unit 40 represent an example of a rearrangement unit.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable storage medium for storing a machine learning program which causes a processor to perform processing for object recognition, the processing comprising:
creating an input data tensor including a local dimension and a universal dimension by partitioning series data into local units, the series data including a plurality of elements, each of the plurality of elements in the series data being logically arranged in a predetermined order; and
performing machine learning by using tensor transformation in which a transformation data tensor obtained by transforming the input data tensor with a transformation matrix is outputted using a neural network, wherein
the machine learning includes
rearranging the transformation matrix so as to maximize a similarity to a matching pattern serving as a reference in the tensor transformation regarding the universal dimension of the input data tensor, and
updating the matching pattern in a process of the machine learning regarding the local dimension of the input data tensor.

2. The non-transitory computer-readable storage medium according to claim 1, wherein
the series data is image data, and
the local unit is determined based on an image size of the image data.

3. The non-transitory computer-readable storage medium according to claim 2, wherein
each of the elements in the local dimension and the universal dimension is a two-dimensional element.

4. The non-transitory computer-readable storage medium according to claim 1, wherein
the series data is gene sequence data, and
the local unit is a unit of a codon.

5. The non-transitory computer-readable storage medium according to claim 4, wherein
the input data tensor is created by determining an input value by using the local dimension and the universal dimension.

6. The non-transitory computer-readable storage medium according to claim 1, the processing further comprising:
creating the input data tensor including the local dimension and the universal dimension by partitioning series data into the local units, the series data being inputted as classification target data;
transforming the created input data tensor into the transformation data tensor by making the input data tensor similar to the matching pattern; and
outputting a result of classification of the series data by inputting an input value in the transformation data tensor to a node in the neural network.

7. A machine learning method implemented by a computer, comprising:
creating an input data tensor including a local dimension and a universal dimension by partitioning series data into local units, the series data including a plurality of elements, each of the plurality of elements in the series data being logically arranged in a predetermined order; and
performing machine learning by using tensor transformation in which a transformation data tensor obtained by transforming the input data tensor with a transformation matrix is outputted using a neural network, wherein
the machine learning includes
rearranging the transformation matrix so as to maximize a similarity to a matching pattern serving as a reference in the tensor transformation regarding the universal dimension of the input data tensor, and
updating the matching pattern in a process of the machine learning regarding the local dimension of the input data tensor.

8. The machine learning method according to claim 7, further comprising:
creating the input data tensor including the local dimension and the universal dimension by partitioning series data into the local units, the series data being inputted as classification target data;

transforming the created input data tensor into the transformation data tensor by making the input data tensor similar to the matching pattern; and outputting a result of classification of the series data by inputting an input value in the transformation data tensor to a node in the neural network.

9. A machine learning apparatus comprising:

a memory; and a processor coupled to the memory, the processor being configured to execute a creation processing that includes creating an input data tensor including a local dimension and a universal dimension by partitioning series data into local units, the series data including a plurality of elements, each of the plurality of elements in the series data being logically arranged in a predetermined order, and execute a machine learning processing that includes performing learning by using tensor transformation in which a transformation data tensor obtained by transforming the input data tensor with a transformation matrix is outputted using a neural network, wherein the machine learning processing is configured to:

execute a rearrangement processing that includes rearranging the transformation matrix so as to maximize a similarity to a matching pattern serving as a reference in the tensor transformation regarding the universal dimension of the input data tensor; and execute an updating processing that includes updating the matching pattern in a process of the machine learning regarding the local dimension of the input data tensor.

10. The machine learning apparatus according to claim 9, wherein the processor is further configured to:

execute a second creation processing configured to create the input data tensor including the local dimension and the universal dimension by partitioning series data into the local units, the series data being inputted as classification target data; and execute an analysis processing configured to transform the created input data tensor into the transformation data tensor by making the input data tensor similar to the matching pattern, and to output a result of classification of the series data by inputting an input value in the transformation data tensor to a node in the neural network.

11. A non-transitory computer-readable storage medium for storing a machine learning program which causes a processor to perform processing, the processing comprising:

creating an input data tensor including a local dimension and a universal dimension by partitioning series data into local units, the series data including a plurality of elements, each of the plurality of elements in the series data being logically arranged in a predetermined order; and transforming the created input data tensor into a transformation data tensor in which the input data tensor is made similar to a matching pattern that optimizes a correspondence relation between an input value in the input data tensor and a node in a neural network; and executing machine-learning processing of the series data by inputting an input value in the transformation data tensor to the node in the neural network.

* * * * *